United States Patent
Reuzeau

(10) Patent No.: US 7,928,288 B2
(45) Date of Patent: Apr. 19, 2011

(54) PLANTS HAVING IMPROVED GROWTH CHARACTERISTICS AND METHOD FOR MAKING THE SAME

(75) Inventor: Christophe Reuzeau, Tocane (FR)

(73) Assignee: CropDesign N.V., Zwijinaarde (BE)

( * ) Notice: Subject to any disclaimer, the term of this patent is extended or adjusted under 35 U.S.C. 154(b) by 542 days.

(21) Appl. No.: 11/632,336

(22) PCT Filed: Jul. 12, 2005

(86) PCT No.: PCT/EP2005/053324
§ 371 (c)(1),
(2), (4) Date: Jul. 5, 2007

(87) PCT Pub. No.: WO2006/005751
PCT Pub. Date: Jan. 19, 2006

(65) Prior Publication Data
US 2007/0245432 A1    Oct. 18, 2007

Related U.S. Application Data

(60) Provisional application No. 60/588,917, filed on Jul. 16, 2004.

(30) Foreign Application Priority Data

Jul. 12, 2004 (EP) .................................... 04103303

(51) Int. Cl.
*C12N 15/82* (2006.01)
*C12N 5/00* (2006.01)
(52) U.S. Cl. ..... 800/278; 800/298; 800/320; 800/320.1; 800/320.2; 800/320.3; 435/410
(58) Field of Classification Search ........................ None
See application file for complete search history.

(56) References Cited

U.S. PATENT DOCUMENTS

2004/0123343 A1 * 6/2004 La Rosa et al. ............... 800/278
2007/0214517 A1 * 9/2007 Alexandrov et al. ......... 800/278

FOREIGN PATENT DOCUMENTS

WO    WO 2004/035732    *    4/2004
WO    WO-2004/035732 A2    4/2004

OTHER PUBLICATIONS

Database UniProt_15.5, Accession No. ARM97791, Oct. 1, 2000, see alignment in office action.*
Roxström-Lindquist, K. et al., "The *Drosophila* Gene *Yippee* Reveals a Novel Family of Putative Zinc Binding Proteins Highly Conserved Among Eukaryotes", Insect Molecular Biology, 2001, vol. 10, No. 1, pp. 77-86.
Farlie, P. et al., "Ypel1: A Novel Nuclear Protein that Induces an Epithelial-like Morphology in Fibroblasts", Genes to Cells, 2001, vol. 6, pp. 619-629.
Hosono, K. et al., "Identification and Characterization of a Novel Gene Family YPEL in a Wide Spectrum of Eukaryotic Species", Gene, 2004, vol. 340, pp. 31-43.

* cited by examiner

*Primary Examiner* — Eileen B O Hara
(74) *Attorney, Agent, or Firm* — Connolly Bove Lodge & Hutz, LLP

(57) ABSTRACT

The present invention concerns a method for improving the growth characteristics of plants by increasing activity in a plant of a YIPPEE-like polypeptide or a homologue thereof. One such method comprises introducing into a plant a YIPPEE-like nucleic acid or variant thereof. The invention also relates to transgenic plants having introduced therein a YIPPEE-like nucleic acid or variant thereof, which plants have improved growth characteristics relative to corresponding wild type plants. The present invention also concerns constructs useful in the methods of the invention.

22 Claims, 10 Drawing Sheets

```
PredictionAY109711.1maize    MGRLF----------------------------------LMHLDGN-  12
PredictionAK109500rice       MGRLF----------------------------------VMHLEGK-  12
At2g40110                    MGRLF----------------------------------VVNLEGK-  12
AB061267Solanum              MGRLF----------------------------------VLTLEGK-  12
At3g11230                    MGRLF----------------------------------LVNLEGK-  12
At3g08990                    MGRLF----------------------------------VIDLEGL-  12
At5g53940                    MGRIF----------------------------------TVELEGR-  12
PredictionAY104347.1maize    MGRLL----------------------------------LVSLPATG  13
At4g27740                    MNVVVGPKIGRKLITGSYVVADVMCSENLVGAIDHALKVFDKMAQAIGPR  50
PredictionAK121352rice       ------------------------------------MVF--MAELVGPR  11
PredictionNM_196100.1rice    MGLLF----------------------------VELLPRHGDGGGPA  19
CDS1522At3g55890             ------------------------------------------------

PredictionAY109711.1maize    --VYSCKHCKTHLGVASDIISKAFQCKHGKAYLHHKVVNVTSGVKE-DRM  59
PredictionAK109500rice       --VYSCKHCHTHLGLSSDIISKSFHCKHGKAYLHNKVVNVTSGVKE-DRM  59
At2g40110                    --IYSCKHCKTHLATYEDIISKSFHCKHGKAYLHNKVANVSIGETE-ERL  59
AB061267Solanum              --IYSCKHCGTHLALSENIVSKSFHCKHGKAYLHSKVVNVTSGEIE-NRM  59
At3g11230                    --SYSCKHCKTNLALCDDVVSKSFQSRHGKAYLHSKVVNVYAGKKE-DRM  59
At3g08990                    --VYSCKYCQTHFAVTNDIISKSFHCKHGRAYLHDNVVNVTVGEKE-HRV  59
At5g53940                    --SYRCRFCRTHLALPDDLVSRSFHCIRGKAYLHNRSVNISMGPLE-ERL  59
PredictionAY104347.1maize    AVIYRCKHCDTHLAYDTDIIARTFRCHNGKAYLHNRIVNVNVGTKEEDRM  63
At4g27740                    --LYSCCNCRNHVGLHDDIISKAFQGHTGRAFLHSHAMNIVVGPKE-DRN  97
PredictionAK121352rice       --VYSCCNCRNHVCLHDDIISKAFQGHNGRAFLHSHAMNVVVGAKE-DRQ  58
PredictionNM_196100.1rice    SAVLKCRRCRVDAASADAILSRDFRGHFGRAYLHDHVVNISLGPNE-DRY  68
CDS1522At3g55890             -------------------------------------------------

PredictionAY109711.1maize    MITGMHTVSDIFCVGCGSIVGWKYDAAHEKGQRYKEGKFILER--YKVSG  107
PredictionAK109500rice       MITGMHTVSDIFCVGCGSIVGWKYEAAHEKSQRYKEGKFILER--YKVSG  107
At2g40110                    MMTGKHTVADIFCVSCGSIVGWKYETAHEKNQKYKEGKSVLER--FKISG  107
AB061267Solanum              MMTGMHTVADIFCVCCGSIVGWKYETAHEKSQKYKEGKSVLER--FKITG  107
At3g11230                    MMTGMHTVVDIYCVKCGSYVGWKYEFAFEKNQKYKEGKSVLER--YKVWG  107
At3g08990                    MITGWHTVADIFCVSCGSLVGWKYEIAYDKSQKYKEGKFILER--FKVLG  107
At5g53940                    MLSGMHTVADIFCCCCGQNVGWKYESAHEKAQKYKEGKFVLER--GRIVD  107
PredictionAY104347.1maize    MTTGLHTVCDIFCVACGAILGWKYLVAFDKSQRYKEGKFILDRSTALAAA  113
At4g27740                    LLTGLHTVADISCVDCNEPLGWKYERAYETSQKYKEGKFIFEK--AKIVK  145
PredictionAK121352rice       LMTGLHTVADIYCNDCREVLGWKYERAYEETQKYKEGKFIFEK--SKIVK  106
PredictionNM_196100.1rice    LMTGLHTVKDIYCSCCQQILGWRYEKAYEESEKYKEGKFILEK--ARMWK  116
CDS1522At3g55890             -------------------------------------------------

PredictionAY109711.1maize    PDGSQYWVP-QDAHLGGSDADDI--  129
PredictionAK109500rice       PDGSHYFVT-HDAHVGGSDVDDV--  129
At2g40110                    PDGSNYWVSSHGRHIGGSDADDA--  130
AB061267Solanum              PDGSHYWAS-HDTHVAGSDADDV--  129
At3g11230                    PDGNNYWVA-QEVEAGDSDTDDA--  129
At3g08990                    PYGGGYDMN-QNEPMTGSDDEE---  128
At5g53940                    EIDLSTEVY-IDTHGSTSDTEDS--  129
PredictionAY104347.1maize    PGDAAADHHHHHARVASSDDEDDHM  138
At4g27740                    EDW----------------------  148
PredictionAK121352rice       ENW----------------------  109
PredictionNM_196100.1rice    EAR----------------------  119
CDS1522At3g55890             -------------------------
```

FIGURE 1

SEQ ID NO 01: At3g55890 mRNA, complete cds ORF 92-457

ACAATTTCCTCCTTCTCCCGTTATAAACTAAAGACTCGATTTTGTGTTGATTGTTCGATTCACG
TAATTAAGGAGATTTTTGGATCAAAAGATGGGTAGGGTTTTTATGGTTGATCTGGAAGGGAACA
TCTACATCTGCAAACTCTGTAAGACCCATCTTTCTACAGACCAAGACATCATGTCCAAGTCTTT
TCAATGCAAGAACGGAAGAGCTTATCTTTTCAACAACGTTGTAAACGTATCTGTTGGAGAGAAA
GAAGACAGAATGATGATAACTGGACTACACAACGTAGTTGACATTTTCTGTGTTGGTTGTGGAT
CAAACGTTGGCTGGAAATACGAGTTTGCACATGAAAAGAGCCAGAAGTATAAGGAAGGAAAATC
TGTTCTTGAATTATACAAGATTTCGGGTCCTCATGATAGCAACGACTTGGTTAGTGATGGAGAT
GATGCTTGATTGAGGCTTTTTCCTTGTCTAGTTATCTCTCTCAGATTTCTTTTAAATTTGTA
CATTCTTGGGCCTAGATTTTAATTCGTTTCAATATGCGTAGTGGAAGACCGGTTTAATAATTAG
GGGTTTTATTTTCAT

SEQ ID NO 02: CDS1522 At3g55890
MGRVFMVDLEGNIYICKLCKTHLSTDQDIMSKSFQCKNGRAYLFNNVVNVSVGEKEDRMMITGL
HNVVDIFCVGCGSNVGWKYEFAHEKSQKYKEGKSVLELYKISGPHDSNDLVSDGDDA

SEQ ID NO 03: At3g08990 mRNA, complete cds ORF 21-407

GGTAGGTGGGTTTGTTCGAAATGGGAAGACTATTCGTGATAGACCTCGAAGGACTGGTTTATAG
CTGCAAGTATTGTCAGACACATTTCGCAGTTACTAATGATATTATCTCAAAGTCATTTCACTGC
AAACACGGAAGGGCTTATCTTTTCGACAATGTTGTCAATGTGACGGTTGGAGAGAAGGAGCATC
GCGTCATGATAACTGGTTGGCACACTGTAGCTGACATCTTCTGTGTTAGCTGTGGCTCTCTTGT
CGGCTGGAAATACGAAATCGCTTACGATAAGTCTCAGAAATACAAGGAAGGAAAATTCATCTTA
GAAAGGTTTAAGGTGCTTGGGCCCTATGGAGGAGGATACGACATGAACCAGAACGAGCCTATGA
CTGGAAGCGATGATGAAGAATAAAAATATGGTATCTCTGTTATTTAACGACCCATTGGAAATAC
TTGGAAAGTGGTCAATGCTTCGTATAGACTATCGGTGACCGGGAAACTCGCCGGGAAAAAATTC
AACATTTTTTCGTGTAAGCGTTCAAAAGAAACCAAATATTCATCATATAAGTAACAAATATAGT
TTTTCTATGAATTTTAAAACTCATATTATAATGCATATCAAGTTGTTAATCGTT

SEQ ID NO 04: At3g08990

MGRLFVIDLEGLVYSCKYCQTHFAVTNDIISKSFHCKHGRAYLFDNVVNVTVGEKEHRVMITGW
HTVADIFCVSCGSLVGWKYEIAYDKSQKYKEGKFILERFKVLGPYGGGYDMNQNEPMTGSDDEE

FIGURE 3

SEQ ID NO 05: At3g11230 mRNA, complete cds ORF 120-509

GTAATATCGTCAAAGAACACTTTATATGATTTTTCTCTATTTTAAAGTTTCTTCCTTTTTCATC
TAAAAATCGGCAGAAAATCCTAACTCCAGTCTTGCATTCTGGGAATAGTTTAGAGATGGGGAGA
TTGTTCTTGGTGAATTTGGAAGGCAAGTCTTACAGTTGTAAGCACTGCAAGACCAATCTTGCTC
TCTGTGATGATGTCGTCTCTAAGTCTTTTCAGTCCCGACATGGGAAAGCTTACCTCTTCAGTAA
GGTAGTGAATGTGTATGCTGGCAAGAAAGAAGATAGGATGATGATGACGGGAATGCATACGGTG
GTCGATATTTACTGTGTCAAATGCGGCTCTTATGTTGGATGGAAATATGAGTTTGCTTTTGAGA
AGAATCAAAAGTACAAGGAAGGAAAATCTGTTCTCGAAAGGTACAAGGTCTGGGGTCCAGATGG
GAACAATTATTGGGTGGCTCAAGAAGTTGAAGCCGGAGACAGCGATACTGATGATGCTTGATTC
TCATCATTCATATCTGATTTGTACATTCCCTCCAACTCTTTCATTTTTCTTTATTCTTTTTCCT
CATTTTGTAAACCATCTATCTTACATTAGAACAGCTTCCGAGACCAATTGTTTGGTCATTGCTG
CAACTACTTTGGACACATAAGTTAAAGATCTCATTATCTTATTTGCA

SEQ ID NO 06: At3g11230

MGRLFLVNLEGKSYSCKHCKTNLALCDDVVSKSFQSRHGKAYLFSKVVNVYAGKKEDRMMMTGM
HTVVDIYCVKCGSYVGWKYEFAFEKNQKYKEGKSVLERYKVWGPDGNNYWVAQEVEAGDSDTDD
A

SEQ ID NO 07: At2g40110 mRNA, complete cds ORF 220-612

AAAGTGAATAATTGAAGAAAAGACGTTATACCTTCCCCATCCACATTTTCTTGCTTAACTGCAG
AACAACACCAAATTCGACCCTATCAAGTTTTGATTCGTGTCTACATAGAAAGAGTCTCAATTGT
TCTGTCCCTGGACTTTTTTTTGTTTCGTTTTTCTTGTTAAGATCGAAAACTCTGTTTTGGTAGA
TTTTTGTGTTCTTGATTTTGATTCAAGATGGGGAGGCTGTTTGTGGTGAATCTTGAAGGGAAGA
TCTATAGCTGCAAACACTGTAAGACTCATCTTGCTACTTATGAAGACATCATCTCCAAGTCTTT
TCACTGCAAGCATGGGAAAGCTTATCTCTTCAATAAGGTTGCCAATGTTTCCATTGGAGAGACT
GAAGAAAGACTGATGATGACTGGTAAACATACTGTGGCTGATATTTTCTGTGTCTCGTGTGGAT
CAATCGTTGGCTGGAAATACGAGACTGCTCATGAGAAGAACCAGAAGTACAAAGAAGGAAAATC
AGTGCTTGAAAGATTTAAGATATCGGGTCCTGATGGGAGCAACTATTGGGTGAGTAGCCATGGA
AGGCATATAGGTGGAAGTGATGCAGATGATGCTTGAATCATCTCTCTCTCTCTATTCTCTGA
TTTGACCATTTCATGTAAATGTAAATTATTCAACCTCCATTCCAATTTCTTGTAATAAGACTAA
CCAATACTCTTTCTTCTCTTGACTTATTATGTCTCAGTAAATAAAAAATCTGATTCTGTCTAAT
GACTATTTATTGGTTTTCTGTGAAACCATC

SEQ ID NO 08: At2g40110

MGRLFVVNLEGKIYSCKHCKTHLATYEDIISKSFHCKHGKAYLENKVANVSIGETEERLMMTGK
HTVADIFCVSCGSIVGWKYETAHEKNQKYKEGKSVLERFKISGPDGSNYWVSSHGRHIGGSDAD
DA

FIGURE 3 (continued)

SEQ ID NO 09: At4g27740 mRNA, complete cds ORF 1-447

ATGAACGTGGTGGTTGGACCGAAGATTGGGAGGAAACTGATAACCGGATCGTATGTAGTGGCAG
ATGTGATGTGCAGTGAGAACTTGGTTGGAGCAATTGATCACGCCTTGAAAGTGTTTGATAAAAT
GGCTCAGGCAATTGGTCCAAGACTGTATAGTTGCTGCAACTGCAGAAACCATGTTGGACTTCAC
GATGATATCATCTCTAAGGCTTTTCAGGGAAGAACTGGGCGAGCCTTCCTGTTCTCCCACGCAA
TGAACATTGTGGTAGGACCTAAAGAAGACCGGAATCTTCTAACTGGTCTACACACCGTGGCTGA
TATATCTTGTGTTGACTGTAACGAACCATTGGGTTGGAAATACGAGCGAGCTTATGAGACCTCA
CAGAAGTACAAGGAGGGCAAGTTCATATTCGAAAAGGCTAAGATTGTCAAGGAGGATTGGTAGA
GCTGAGGAACATGATGAATTCATTATTGGATTGGCTCAAAAATGTATATAGATAAAATTTGGCT
TTGTGATTTCACAAGTCATCATCAGCCATTTTTCCAGTTCTTCATTGTCTCTCTCTGTATGTTA
ATTATGTCGTCTCTTGTGTTCAAACTATGGATTTGTTCGAACAAGGTTTCTCTGTTAATAAAGA
TGTTAATAGCTTCTC

SEQ ID NO 10: At4g27740

MNVVVGPKIGRKLITGSYVVADVMCSENLVGAIDHALKVFDKMAQAIGPRLYSCCNCRNHVGLH
DDIISKAFQGRTGRAFLFSHAMNIVVGPKEDRNLLTGLHTVADISCVDCNEPLGWKYERAYETS
QKYKEGKFIFEKAKIVKEDW

SEQ ID NO 11: At5g53940 mRNA, complete cds ORF 22-411

AGATAGAACAGTGAAGAAGAAATGGGAAGGATATTCACGGTGGAGCTTGAAGGAAGATCTTACA
GATGCAGGTTCTGCAGAACCCATCTCGCTCTTCCCGATGATCTTGTCTCTCGGTCGTTTCATTG
CCGTAGAGGAAAGGCTTACCTCTTCAACCGTTCGGTGAACATAAGTATGGGTCCTCTAGAGGAA
AGACTGATGCTTTCCGGTATGCACACCGTAGCTGACATTTTCTGCTGCTGTTGTGGACAGAATG
TTGGCTGGAAATACGAATCAGCGCACGAGAAAGCTCAGAAGTATAAAGAAGGCAAATTTGTTCT
GGAAAGAGGAAGGATCGTGGATGAAATCGATTTATCAACTGAGGTTTATATCGATACTCATGGT
AGCACAAGCGACACAGAAGATTCTTAAATGTTACCTTTTTTCTGTGTGTTTGTCAAGAGCAGAG
CTTGTTAGTGTAGAAATCTGTAGCATGTTTATAGAGATGTGTATCAAACTTGTTGTGTTGTTTT
TATATCTCGTAGAAATTTTATGTGAATTCGAATCTTTATTTTAAATCCAATAAAAACTCATT

SEQ ID NO 12: At5g53940
MGRIFTVELEGRSYRCRFCRTHLALPDDLVSRSFHCRRGKAYLFNRSVNISMGPLEERLMLSGM
HTVADIFCCCCGQNVGWKYESAHEKAQKYKEGKFVLERGRIVDEIDLSTEVYIDTHGSTSDTED
S

FIGURE 3 (continued)

SEQ ID NO 13: Solanum tuberosum mRNA for yippee-like protein, complete cds ORF 85-474

CCGAAACAAAAACTATTACCCCTTTTTGGACAAGTCCTTTTCCATTTTGGTTCTTCAATTTTCT
TGTGATCTCAAAAATCTTTGATGGGGAGATTATTTGTGTTGACTCTTGAAGGCAAGATCTACAG
CTGCAAGCACTGTGGAACTCATCTTGCCCTTTCTGAAAACATTGTTTCCAAGTCTTTCCACTGC
AAACATGGGAAGGCATACCTTTTCAGTAAAGTGGTGAATGTCACTTCTGGCGAGATAGAAAATA
GAATGATGATGACTGGTATGCACACTGTGGCAGACATTTTCTGCGTCTGTTGTGGGTCAATTGT
TGGATGGAAATATGAGACCGCCCATGAGAAGAGCCAAAAGTACAAAGAAGGAAAATCAGTGCTT
GAGCGGTTTAAGATTACTGGACCTGATGGAAGCCATTACTGGGCTAGTCATGATACTCATGTTG
CAGGAAGTGATGCTGATGATGTTTGATCACCATTCAGAACAAAAATTCTATCCAAAAATGTACA
TTCTTTAACCCACCACCCTATTAGTTCTTTATGGACCATTGGATTCTTGAATAGCTTAAGCTCT
ACAACTTCTTTAAGCTTGTCCTCTATTGTGTATGATGATATGGAAGCACCATGTGTTGTTGCAA
ACTAACACGACCATCTGCCTGTATTTGTTTGCAATGACAAGACATTACTAGTAGCAACCACTCT
GCTTTCATTGCTTCGAAAAAAAAAAAAAAAAAAAAAA

SEQ ID NO 14: Solanum tuberosum yippee-like protein

MGRLFVLTLEGKIYSCKHCGTHLALSENIVSKSFHCKHGKAYLFSKVVNVTSGEIENRMMMTGM
HTVADIFCVCCGSIVGWKYETAHEKSQKYKEGKSVLERFKITGPDGSHYWASHDTHVAGSDADD
V

SEQ ID NO 15: AY109711.1 Zea mays mRNA sequence
AAGCGTGCAGCTATTCGGTTATTTAAGAGTGACGTTGGAACCGAACACACAATACAATGCAGAT
TTGTACATACTGCCCTCGCTTGACACCCAGGTCGACCAGACACTTGAGAAATTTACTTTACTTA
TTTGGTCACTAGTGCTTGGCATACAACTCAGATGGACTTATAAGCAACACAGGTTACGCACATA
TACAGCGGTAACATCTAATGACTTCCAGAAGCAATAGGAGGGATATGATNNNNNNNNCATGTCA
CCTGGAACAGCAACAATTTACGCCGGCGAATTATTTCAATGGAGCAATCCCCGGCTGTCGGCTG
CCTAAAGAGCAACGCCACCCAGGTTATTTACAGGGGATCAACGACAGGCTTGAGCTTGTTGGAT
CGTGTTTTATATGTCATCGGCGTCGCTTCCGCCCAAGTGAGCATCTTGTGGAACCCAGTATTGG
CTTCCGTCAGGGCCCGACACCTTGTACCTCTCCAGAATAAACTTGCCTTCCTTGTATCTCTGGC
CCTTCTCATGTGCCGCATCATATTTCCACCCAACTATGGATCCACAGCCAACACAGAAGATATC
AGAAACAGTATGCATTCCTGTGATCATCATGCGGTCTTCTTTTACTCCAGAAGTCACGTTGACA
ACCTTATGGAAGAGGTACGCCTTGCCGTGCTTGCACTGGAAGGCCTTGGAGATGATGTCGCTGG
CAACGCCGAGGTGGGTCTTGCAGTGTTTGCAGCTGTAGACGTTGCCGTCCAGGTGCATCAGGAA
CAGGCGCCCCATCGCCGCCTTCTCTCCCACCTGCCGCAACTCCGCTCCAACCCCTCTCTCTCGG
CTTCTCGTCAATTCCACCCAGCGCACGGCGTCGAGGGCCACTCTAGCCCCGATCGCCGCGGCTC
GAAATCCCCTCTTCCGGCTTCCTCGGATCGGAGACTGGGAGCGGGAGTTGTTTATTGNNNNNNN
NNNNNNNNNNNNNNNNNNNGCGGCGGTGGTATCTGGTATGGTGCGAATGTGCGATGTGTCAGCGA
GCGTCGTG

FIGURE 3 (continued)

SEQ ID NO 16: Prediction AY109711.1maize

MGRLFLMHLDGNVYSCKHCKTHLGVASDIISKAFQCKHGKAYLPHKVVNVTSGVKEDRMMITGM
HTVSDIFCVGCGSIVGWKYDAAHEKGQRYKEGKFILERYKVSGPDGSQYWVPQDAHLGGSDADD
I

SEQ ID NO 17: AY104347.1 Zea mays mRNA sequence

GCACGAGAACAAACCCCGCACGACTCGTTCTCATTCCACTCTCCAACGCGCACCGGGCGGTTTT
TCGTTCCTTTCTTTTTTTTTCCCCTCTTCCCCTTCCCCTTCTCCTTCCAGCGGCGCTCAGGCCA
CCGCCGGCCAATCCCATCACCCGCCGGATAGGGATCGACCCGTTCGTTGATTGGCGCGCGCCTG
CGATCGATCGATTGGATTGCAGGGTTAGGGCGGCCGCCGTCGAGATAGATCGATCCATCCATCG
ATCGAATTGGTTTTGTTGGTGGATCGGAGATATTCATTCGGGTCCATGGGTCGGCTGCTGCTGG
TGAGCCTCCCGGCGACGGGCGCCGTCATCTACCGCTGCAAGCACTGCGACACCCACCTCGCCTA
CGACACCGACATCATCGCAAGGACGTTCCGCTGCAAGAACGGCAAGGCCTACCTCTTCAACAGG
ATCGTGAATGTGAATGTTGGTACGAAGGAGGAGGACCGGATGATGACGACGGGCCTGCACACCG
TGTGCGACATCTTCTGCGTCGCCTGCGGAGCCATACTCGGCTGGAAATACCTCGTCGCCTTCGA
CAAGAGCCAGAGGTACAAGGAAGGCAAGTTCATCCTCGACAGGTCCACCGCCTTGGCAGCCGCT
CCTGGTGATGCCGCTGCTGACCACCACCACCACCACGCTCGCGTAGCAAGCTCCGATGACGAAG
ATGACCATATGTGAATGATGATGATGATGAATGTCATCTGCATTGCATTCACCATAATCCCTTG
CTATCTGTAAATACTCTACTCCGCTTGTTGTAGTCGTTCGTCGTAAAGCACCTATATGTTTCCA
TTTGTTCAACCTATCAGACTATGATATGATCAGCAAGTAAGGTCCATTTGTTTGGATGCAGCGA
CAGTTACAAACAAAAAAATTAAAA

SEQ ID NO 18: Prediction AY104347.1 maize

MGRLLLVSLPATGAVIYRCKHCDTHLAYDTDIIARTFRCKNGKAYLFNRIVNVNVGTKEEDRMM
TTGLHTVCDIFCVACGAILGWKYLVAFDKSQRYKEGKFILDRSTALAAAPGDAAADHHHHHARV
ASSDDEDDHM

SEQ ID NO 19: NM_196100.1 Oryza sativa

ATGGGCTGCTGTTCGTGGAGCTGCTCCCGCGGCACGGCGACGGGGGAGGCCCCGCGTCGGCGG
TGCTCAAGTGCCGCCGGTGCCGCGTCGACGCCGCCTCCGCCGACGCCATCCTCTCACGGGACTT
CCGCGGCCGATTCGGCCGCGCCTACCTCTTCGACCACGTGGTGAATATATCCTTAGGGCCTAAT
GAGGATCGGTATCTGATGACCGGACTGCATACGGTGAAAGATATCTACTGTAGCTGTTGCCAGC
AAATTCTCGGCTGGAGATATGAGAAAGCATACGAAGAGAGCGAGAAGTACAAGGAAGGCAAGTT
CATCCTGGAGAAGGCCAGGATGTGGAAAGAAGCCCGGTGA

FIGURE 3 (continued)

SEQ ID NO 20: Prediction NM_196100.1

MGLLFVELLPRHGDGGGPASAVLKCRRCRVDAASADAILSRDFRGRFGRAYLFDHVVNISLGPN
EDRYLMTGLHTVKDIYCSCCQQILGWRYEKAYEESEKYKEGKFILEKARMWKEAR

SEQ ID NO 21: AK121352.1 Oryza sativa

GATTTTTCTTCTCCCAAACTCCGGCGACTCCTCCGCTAATCCCCTCCGGCGCCGCCTCCTCTCC
GCTCCCCGCGCCCCCCACCTCCGGTCACGCCCGATCGGATTGGTTGAGTTGCCTCGAGGGATTT
TTGCTCTCGAGGTATGGTGTTCATGGCGGAGCTGGTGGGTCCGCGGGTGTACAGCTGCTGCAAC
TGCCGGAACCACGTCTGCCTCCACGACGACATCATCTCCAAGGCTTTTCAGGGGAGGAATGGCC
GTGCCTTTCTGTTCTCTCATGCCATGAATGTTGTTGTGGGCGCGAAGGAGGACAGGCAACTTAT
GACGGGGCTTCACACTGTTGCTGATATCTATTGCAATGATTGCCGGGAGGTGTTGGGCTGGAAG
TACGAGAGAGCCTATGAGGAAACACAGAAGTACAAGGAAGGGAAGTTCATATTTGAGAAGTCAA
AAATCGTCAAAGAGAACTGGTAGAATCCAAAAGATTAGGCACTCCAAACTTTCTTTAGAGGATG
AAACATTCACTGTTCCAAGGTTATCAGTGTGTTCTGGTTCTTTATGTCTTTGTAAATATCAGTC
ATCCACAAGTTTTAATCTTAAGTCTGCCTGTTCTTGCCTTGCCGTGAAGTGTAAATTGTTCTTG
CTCCCGTTTCTTTCTGTGAATAACATATGGCCTGTGGGTATTTGTTCTTGAACCATGTGTGCTA
ATGTGCGTAATTTTATAGGTACTAAAAGAATGTTTGTATCTTTCTCCTGCACAAGAATACCGCG
TGGAGATTTACAGTCAAATATAATCTGACATGATTTAATCAAAATTTGTTGGGAAGTTGTGAAG
TAAG

SEQ ID NO 22: Prediction AK121352 rice

MVFMAELVGPRVYSCCNCRNHVCLHDDIISKAFQGRNGRAFLFSHAMNVVVGAKEDRQLMTGLH
TVADIYCNDCREVLGWKYERAYEETQKYKEGKFIFEKSKIVKENW

SEQ ID NO 23: AK109500.1 Oryza sativa

GCTGCTTTTGCTTCGGTCACCCGGTCAGTGCTGCAGACAAGCCACCCCCTTCCTCGCGTAGACT
GCTCCCCCCACAAACAAAAGCAATCCTAATCTCGGATTCGAGGCGAACGAGCGGCGGCGAGGGA
GGGGGACTAGCGGCGATCGCGATTGGAGTCGGGTGGACACCGATCGCGGCGGCGCTCTGGGGGA
TCGGGGTGTGGAATCGAGGGGGAGGGAGGAGGAGACGGAGGCGATGGGCGGCTGTTCGTGATG
CACCTGGAAGGGAAGGTGTACAGCTGCAAGCACTGCCACACGCACCTCGGCCTCTCCTCCGACA
TCATCTCCAAGTCCTTCCATTGCAAGCACGGGAAGGCGTACCTCTTCAATAAGGTTGTCAATGT
GACTTCTGGAGTAAAAGAGGATCGCATGATGATAACCGGAATGCATACTGTGTCTGATATCTTC
TGTGTTGGCTGCGGATCCATTGTTGGATGGAAATATGAAGCTGCACATGAGAAGAGCCAGAGGT
ACAAGGAAGGGAAATTTATTTTAGAGAGGTATAAGGTGTCTGGTCCTGATGGCAGCCACTACTT
TGTTACACATGATGCTCATGTTGGGGAAGCGACGTGGACGACGTATGAAGCACAACTCGACAT
GCTCAAGCCTTATCCATGTAATCCATGTAAATAACCCAAGTGTTTGTTGGTCTTAGTTACCCGG
GGATTTGCTTCCATTCAGAGCAACCCCAGCGTAATTGTTGTCCTAGATGACCTAATATCCTATC
ATCTTCCTTCAGGAGTTCAGGTTATTATTGGGTGTTACCGTCTGTATATGCATGTAACCAGTGA
TGCCTGTAGTAGCCCCCTAAAAGCTGTTGTAATCCTGGAATGTATCTCAGGCCCTAATGACTAA
ATAAAATTCTGCTTCTC

FIGURE 3 (continued)

SEQ ID NO 24: Prediction AK109500 rice

MGRLFVMHLEGKVYSCKHCHTHLGLSSDIISKSFHCKHGKAYLENKVVNVTSGVKEDRMMITGM
HTVSDIFCVGCGSIVGWKYEAAHEKSQRYKEGKFILERYKVSGPDGSHYFVTHDAHVGGSDVDD
V

SEQ ID NO 25: Oryza staiva GOS2 promoter

```
aatccgaaaagtttctgcaccgttttcaccccctaactaacaatataqggaacgtgtgctaaat
ataaaatgagaccttatatatgtagcgctgataactagaactatgcaagaaaaactcatccacc
tactttagtggcaatcgggctaaataaaaagagtcgctacactagtttcgttttccttagtaa
ttaagtgggaaaatgaaatcattattgcttagaatatacgttcacatctctgtcatgaagttaa
attattcgaggtagccataattgtcatcaaactcttcttgaataaaaaaatctttctagctgaa
ctcaatgggtaaagagagagatttttttttaaaaaaatagaatgaagatattctgaacgtattgg
caaagatttaaacatataattatataattttatagtttgtgcattcgtcatatcgcacatcatt
aaggacatgtcttactccatcccaattttttatttagtaattaaagacaattgacttatttttat
tatttatcttttttcgattagatgcaaggtacttacgcacacactttgtgctcatgtgcatgtg
tgagtgcacctcctcaatacacgttcaactagcaacacatctctaatatcactcgcctatttaa
tacatttaggtagcaatatctgaattcaagcactccaccatcaccagaccacttttaataatat
ctaaaatacaaaaaataattttacagaatagcatgaaaagtatgaaacgaactatttaggtttt
tcacatacaaaaaaaaaagaattttgctcgtgcgcgagcgccaatctcccatattgggcacac
aggcaacaacagagtggctgcccacagaacaacccacaaaaaacgatgatctaacggaggacag
caagtccgcaacaaccttttaacagcaggctttgcggccaggagagaggaggagaggcaaagaa
aaccaagcatcctcctcctcccatctataaattcctccccctttttccctctctatataggag
gcatccaagccaagaagagggagagcaccaaggacacgcgactagcagaagccgagcgaccgcc
ttcttcgatccatatcttccggtcgagttcttggtcgatctcttccctcctccacctcctcctc
acagggtatgtgcccttcggttgttcttggatttattgttctaggttgtgtagtacgggcgttg
atgttaggaaaggggatctgtatctgtgatgattcctgttcttggatttgggatagaggggttc
ttgatgttgcatgttatcggttcggtttgattagtagtatggttttcaatcgtctggagagctc
tatggaaatgaaatggtttagggtacggaatcttgcgattttgtgagtaccttttgtttgaggt
aaaatcagagcaccggtgattttgcttggtgtaataaaagtacggttgtttggtcctcgattct
ggtagtgatgcttctcgatttgacgaagctatcctttgtttattccctattgaacaaaaataat
ccaactttgaagacggtcccgttgatgagattgaatgattgattcttaagcctgtccaaaattt
cgcagctggcttgtttagatacagtagtccccatcacgaaattcatggaaacagttataatcct
caggaacaggggattccctgttcttccgatttgctttagtcccagaatttttttttcccaaatat
cttaaaaagtcactttctggttcagttcaatgaattgattgctacaaataatgcttttatagcg
ttatcctagctgtagttcagttaataggtaatacccctatagtttagtcaggagaagaacttat
ccgatttctgatctccattttaattatatgaaatgaactgtagcataagcagtattcatttgg
attatttttttattagctctcacccttcattattctgagctgaaagtctggcatgaactgtc
ctcaattttgttttcaaattcacatcgattatctatgcattatcctcttgtatctacctgtaga
agtttcttttggttattccttgactgcttgattacagaaagaaatttatgaagctgtaatcgg
gatagttatactgcttgttcttatgattcatttcctttgtgcagttcttggtgtagcttgccac
tttcaccagcaaagttc
```

FIGURE 3 (continued)

SEQ ID NO 26: forward primer prm03198 ggggacaagtttgtacaaaaaagcaggcttcacaatgggtagggttttttatggttgatc

SEQ ID NO 27: reverse primer prm03199 ggggaccact tgtacaaga aagctgggta atcaagcatc atctccatca ctaac

FIGURE 3 (continued)

SEQUENCE LISTING

```
<160> NUMBER OF SEQ ID NOS: 30

<210> SEQ ID NO 1
<211> LENGTH: 591
<212> TYPE: DNA
<213> ORGANISM: Arabidopsis thaliana

<400> SEQUENCE: 1
acaatttcct ccttctcccg ttataaacta aagactcgat tttgtgttga ttgttcgatt      60
cacgtaatta aggagatttt tggatcaaaa gatgggtagg gtttttatgg ttgatctgga     120
agggaacatc tacatctgca aactctgtaa gacccatctt tctacagacc aagacatcat     180
gtccaagtct tttcaatgca agaacggaag agcttatctt ttcaacaacg ttgtaaacgt     240
atctgttgga gagaaagaag acagaatgat gataactgga ctacacaacg tagttgacat     300
tttctgtgtt ggttgtggat caaacgttgg ctggaaatac gagtttgcac atgaaaagag     360
ccagaagtat aaggaaggaa aatctgttct tgaattatac aagatttcgg gtcctcatga     420
tagcaacgac ttggttagtg atggagatga tgcttgattg aggcttttc cttgtctagt      480 tatctctctc tcagatttct tttaaatttg tacattcttg ggcctagatt ttaattcgtt     540
tcaatatgcg tagtggaaga ccggtttaat aattagggt tttattttca t              591

<210> SEQ ID NO 2
<211> LENGTH: 121
<212> TYPE: PRT
<213> ORGANISM: Arabidopsis thaliana
```

<400> SEQUENCE: 2

Met Gly Arg Val Phe Met Val Asp Leu Glu Gly Asn Ile Tyr Ile Cys
1               5                   10                  15

Lys Leu Cys Lys Thr His Leu Ser Thr Asp Gln Asp Ile Met Ser Lys
            20                  25                  30

Ser Phe Gln Cys Lys Asn Gly Arg Ala Tyr Leu Phe Asn Asn Val Val
        35                  40                  45

Asn Val Ser Val Gly Glu Lys Glu Asp Arg Met Met Ile Thr Gly Leu
    50                  55                  60

His Asn Val Val Asp Ile Phe Cys Val Gly Cys Gly Ser Asn Val Gly
65                  70                  75                  80

Trp Lys Tyr Glu Phe Ala His Glu Lys Ser Gln Lys Tyr Lys Glu Gly
                85                  90                  95

Lys Ser Val Leu Glu Leu Tyr Lys Ile Ser Gly Pro His Asp Ser Asn
            100                 105                 110

Asp Leu Val Ser Asp Gly Asp Asp Ala
            115                 120

<210> SEQ ID NO 3
<211> LENGTH: 630
<212> TYPE: DNA
<213> ORGANISM: Arabidopsis thaliana

<400> SEQUENCE: 3
ggtaggtggg tttgttcgaa atgggaagac tattcgtgat agacctcgaa ggactggttt      60
atagctgcaa gtattgtcag acacatttcg cagttactaa tgatattatc tcaaagtcat     120
ttcactgcaa acacggaagg gcttatcttt tcgacaatgt tgtcaatgtg acggttggag     180
agaaggagca tcgcgtcatg ataactggtt ggcacactgt agctgacatc ttctgtgtta     240
gctgtggctc tcttgtcggc tggaaatacg aaatcgctta cgataagtct cagaaataca     300
aggaaggaaa attcatctta gaaaggttta aggtgcttgg gccctatgga ggaggatacg     360
acatgaacca gaacgagcct atgactggaa gcgatgatga agaataaaaa tatggtatct     420
ctgttatttta acgacccatt ggaaatactt ggaaagtggt caatgcttcg tatagactat     480
cggtgaccgg gaaactcgcc gggaaaaaat tcaacatttt ttcgtgtaag cgttcaaaag     540
aaaccaaata ttcatcatat aagtaacaaa tatagttttt ctatgaattt taaaactcat     600
attataatgc atatcaagtt gttaatcgtt                                      630

<210> SEQ ID NO 4
<211> LENGTH: 128
<212> TYPE: PRT
<213> ORGANISM: Arabidopsis thaliana

<400> SEQUENCE: 4

Met Gly Arg Leu Phe Val Ile Asp Leu Glu Gly Leu Val Tyr Ser Cys
1               5                   10                  15

Lys Tyr Cys Gln Thr His Phe Ala Val Thr Asn Asp Ile Ile Ser Lys
            20                  25                  30

Ser Phe His Cys Lys His Gly Arg Ala Tyr Leu Phe Asp Asn Val Val
        35                  40                  45

Asn Val Thr Val Gly Glu Lys Glu His Arg Val Met Ile Thr Gly Trp
    50                  55                  60

His Thr Val Ala Asp Ile Phe Cys Val Ser Cys Gly Ser Leu Val Gly
65                  70                  75                  80

```
Trp Lys Tyr Glu Ile Ala Tyr Asp Lys Ser Gln Lys Tyr Lys Glu Gly
                85                  90                  95
Lys Phe Ile Leu Glu Arg Phe Lys Val Leu Gly Pro Tyr Gly Gly Gly
            100                 105                 110
Tyr Asp Met Asn Gln Asn Glu Pro Met Thr Gly Ser Asp Asp Glu Glu
        115                 120                 125
```

<210> SEQ ID NO 5
<211> LENGTH: 687
<212> TYPE: DNA
<213> ORGANISM: Arabidopsis thaliana

<400> SEQUENCE: 5

```
gtaatatcgt caaagaacac tttatatgat ttttctctat tttaaagttt cttcctttt      60
catctaaaaa tcggcagaaa atcctaactc cagtcttgca ttctgggaat agtttagaga    120
tggggagatt gttcttggtg aatttggaag gcaagtctta cagttgtaag cactgcaaga    180
ccaatcttgc tctctgtgat gatgtcgtct ctaagtcttt tcagtcccga catgggaaag    240
cttacctctt cagtaaggta gtgaatgtgt atgctggcaa gaaagaagat aggatgatga    300
tgacgggaat gcatacggtg gtcgatattt actgtgtcaa atgcggctct tatgttggat    360
ggaaatatga gtttgctttt gagaagaatc aaaagtacaa ggaaggaaaa tctgttctcg    420
aaaggtacaa ggtctggggt ccagatggga acaattattg ggtggctcaa gaagttgaag    480
ccggagacag cgatactgat gatgcttgat tctcatcatt catatctgat ttgtacattc    540
cctccaactc tttcattttt ctttattctt tttcctcatt ttgtaaacca tctatcttac    600
attgaaacag cttccgagac caattgtttg gtcattgctg caactacttt ggacacataa    660
gttaaagatc tcattatctt atttgca                                        687
```

<210> SEQ ID NO 6
<211> LENGTH: 129
<212> TYPE: PRT
<213> ORGANISM: Arabidopsis thaliana

<400> SEQUENCE: 6

```
Met Gly Arg Leu Phe Leu Val Asn Leu Glu Gly Lys Ser Tyr Ser Cys
 1               5                  10                  15
Lys His Cys Lys Thr Asn Leu Ala Leu Cys Asp Asp Val Val Ser Lys
             20                  25                  30
Ser Phe Gln Ser Arg His Gly Lys Ala Tyr Leu Phe Ser Lys Val Val
         35                  40                  45
Asn Val Tyr Ala Gly Lys Lys Glu Asp Arg Met Met Met Thr Gly Met
     50                  55                  60
His Thr Val Val Asp Ile Tyr Cys Val Lys Cys Gly Ser Tyr Val Gly
 65                  70                  75                  80
Trp Lys Tyr Glu Phe Ala Phe Glu Lys Asn Gln Lys Tyr Lys Glu Gly
                 85                  90                  95
Lys Ser Val Leu Glu Arg Tyr Lys Val Trp Gly Pro Asp Gly Asn Asn
            100                 105                 110
Tyr Trp Val Ala Gln Glu Val Glu Ala Gly Asp Ser Asp Thr Asp Asp
        115                 120                 125
Ala
```

<210> SEQ ID NO 7
<211> LENGTH: 798
<212> TYPE: DNA
<213> ORGANISM: Arabidopsis thaliana

<400> SEQUENCE: 7

```
aaagtgaata attgaagaaa agacgttata ccttcccccat ccacattttc ttgcttaact      60
gcagaacaac accaaattcg accctatcaa gttttgattc gtgtctacat agaaagagtc     120
tcaattgttc tgtccctgga ctttttttg tttcgttttt cttgttaaga tcgaaaactc      180
tgttttggta gattttgtg ttcttgattt tgattcaaga tggggaggct gtttgtggtg      240
aatcttgaag ggaagatcta tagctgcaaa cactgtaaga ctcatcttgc tacttatgaa     300
gacatcatct ccaagtcttt tcactgcaag catgggaaag cttatctctt caataaggtt     360
gccaatgttt ccattggaga gactgaagaa agactgatga tgactggtaa acatactgtg     420
gctgatattt tctgtgtctc gtgtggatca atcgttggct ggaaatacga gactgctcat     480
gagaagaacc agaagtacaa agaaggaaaa tcagtgcttg aaagatttaa gatatcgggt     540
cctgatggga gcaactattg ggtgagtagc catggaaggc atataggtgg aagtgatgca     600
gatgatgctt gaatcatctc tctctctctc tattctctga tttgaccatt tcatgtaaat     660
gtaaattatt caacctccat tccaatttct tgtaataaga ctaaccaata ctctttcttc    720
tcttgactta ttatgtctca gtaaataaaa aatctgattc gtctaatga ctatttattg      780
gttttctgtg aaaccatc                                                   798
```

<210> SEQ ID NO 8
<211> LENGTH: 130
<212> TYPE: PRT
<213> ORGANISM: Arabidopsis thaliana

<400> SEQUENCE: 8

```
Met Gly Arg Leu Phe Val Val Asn Leu Glu Gly Lys Ile Tyr Ser Cys
1               5                   10                  15
Lys His Cys Lys Thr His Leu Ala Thr Tyr Glu Asp Ile Ile Ser Lys
                20                  25                  30
Ser Phe His Cys Lys His Gly Lys Ala Tyr Leu Phe Asn Lys Val Ala
            35                  40                  45
Asn Val Ser Ile Gly Glu Thr Glu Glu Arg Leu Met Met Thr Gly Lys
        50                  55                  60
His Thr Val Ala Asp Ile Phe Cys Val Ser Cys Gly Ser Ile Val Gly
65                  70                  75                  80
Trp Lys Tyr Glu Thr Ala His Glu Lys Asn Gln Lys Tyr Lys Glu Gly
                85                  90                  95
Lys Ser Val Leu Glu Arg Phe Lys Ile Ser Gly Pro Asp Gly Ser Asn
                100                 105                 110
Tyr Trp Val Ser Ser His Gly Arg His Ile Gly Gly Ser Asp Ala Asp
            115                 120                 125
Asp Ala
    130
```

<210> SEQ ID NO 9
<211> LENGTH: 655
<212> TYPE: DNA
<213> ORGANISM: Arabidopsis thaliana

<400> SEQUENCE: 9

```
atgaacgtgg tggttggacc gaagattggg aggaaactga taaccggatc gtatgtagtg      60
gcagatgtga tgtgcagtga gaacttggtt ggagcaattg atcacgcctt gaaagtgttt     120
gataaaatgg ctcaggcaat tggtccaaga ctgtatagtt gctgcaactg cagaaaccat     180
```

```
gttggacttc acgatgatat catctctaag gcttttcagg gaagaactgg gcgagccttc    240
ctgttctccc acgcaatgaa cattgtggta ggacctaaag aagaccggaa tcttctaact    300
ggtctacaca ccgtggctga tatatcttgt gttgactgta acgaaccatt gggttggaaa    360
tacgagcgag cttatgagac ctcacagaag tacaaggagg gcaagttcat attcgaaaag    420
gctaagattg tcaaggagga ttggtagagc tgaggaacat gatgaattca ttattggatt    480
ggctcaaaaa tgtatataga taaaatttgg ctttgtgatt tcacaagtca tcatcagcca    540 ttttccagt tcttcattgt ctctctctgt atgttaatta tgtcgtctct tgtgttcaaa     600
ctatggattt gttcgaacaa ggtttctctg ttaataaaga tgttaatagc ttctc         655

<210> SEQ ID NO 10
<211> LENGTH: 148
<212> TYPE: PRT
<213> ORGANISM: Arabidopsis thaliana

<400> SEQUENCE: 10

Met Asn Val Val Val Gly Pro Lys Ile Gly Arg Lys Leu Ile Thr Gly
1               5                   10                  15

Ser Tyr Val Val Ala Asp Val Met Cys Ser Glu Asn Leu Val Gly Ala
            20                  25                  30

Ile Asp His Ala Leu Lys Val Phe Asp Lys Met Ala Gln Ala Ile Gly
        35                  40                  45

Pro Arg Leu Tyr Ser Cys Cys Asn Cys Arg Asn His Val Gly Leu His
    50                  55                  60

Asp Asp Ile Ile Ser Lys Ala Phe Gln Gly Arg Thr Gly Arg Ala Phe
65                  70                  75                  80

Leu Phe Ser His Ala Met Asn Ile Val Val Gly Pro Lys Glu Asp Arg
                85                  90                  95

Asn Leu Leu Thr Gly Leu His Thr Val Ala Asp Ile Ser Cys Val Asp
            100                 105                 110

Cys Asn Glu Pro Leu Gly Trp Lys Tyr Glu Arg Ala Tyr Glu Thr Ser
        115                 120                 125

Gln Lys Tyr Lys Glu Gly Lys Phe Ile Phe Glu Lys Ala Lys Ile Val
    130                 135                 140

Lys Glu Asp Trp
145

<210> SEQ ID NO 11
<211> LENGTH: 574
<212> TYPE: DNA
<213> ORGANISM: Arabidopsis thaliana

<400> SEQUENCE: 11
agatagaaca gtgaagaaga aatgggaagg atattcacgg tggagcttga aggaagatct     60
tacagatgca ggttctgcag aacccatctc gctcttcccg atgatcttgt ctctcggtcg    120
tttcattgcc gtagaggaaa ggcttacctc ttcaaccgtt cggtgaacat aagtatgggt    180
cctctagagg aaagactgat gctttccggt atgcacaccg tagctgacat ttctgctgc     240 tgttgtggac agaatgttgg ctggaaatac gaatcagcgc acgagaaagc tcagaagtat    300
aaagaaggca aatttgttct ggaaagagga aggatcgtgg atgaaatcga tttatcaact    360
gaggtttata tcgatactca tggtagcaca agcgacacag aagattctta aatgttacct    420
tttttctgtg tgtttgtcaa gagcagagct tgttagtgta gaaatctgta gcatgtttat    480
agagatgtgt atcaaacttg ttgtgttgtt tttatatctc gtagaaattt tatgtgaatt    540
```

```
cgaatcttta ttttaaatcc aataaaaact catt                                    574
```

<210> SEQ ID NO 12
<211> LENGTH: 129
<212> TYPE: PRT
<213> ORGANISM: Arabidopsis thaliana

<400> SEQUENCE: 12

```
Met Gly Arg Ile Phe Thr Val Glu Leu Glu Gly Arg Ser Tyr Arg Cys
1               5                   10                  15

Arg Phe Cys Arg Thr His Leu Ala Leu Pro Asp Asp Leu Val Ser Arg
            20                  25                  30

Ser Phe His Cys Arg Arg Gly Lys Ala Tyr Leu Phe Asn Arg Ser Val
        35                  40                  45

Asn Ile Ser Met Gly Pro Leu Glu Glu Arg Leu Met Leu Ser Gly Met
    50                  55                  60

His Thr Val Ala Asp Ile Phe Cys Cys Cys Gly Gln Asn Val Gly
65                  70                  75                  80

Trp Lys Tyr Glu Ser Ala His Glu Lys Ala Gln Lys Tyr Lys Glu Gly
                85                  90                  95

Lys Phe Val Leu Glu Arg Gly Arg Ile Val Asp Glu Ile Asp Leu Ser
            100                 105                 110

Thr Glu Val Tyr Ile Asp Thr His Gly Ser Thr Ser Asp Thr Glu Asp
        115                 120                 125

Ser
```

<210> SEQ ID NO 13
<211> LENGTH: 741
<212> TYPE: DNA
<213> ORGANISM: Solanum tuberosum

<400> SEQUENCE: 13

```
ccgaaacaaa aactattacc ccttttttgga caagtccttt tccatttttgg ttcttcaatt     60
ttcttgtgat ctcaaaaatc tttgatgggg agattatttg tgttgactct tgaaggcaag    120
atctacagct gcaagcactg tggaactcat cttgcccttt ctgaaaacat tgtttccaag    180
tctttccact gcaaacatgg gaaggcatac cttttcagta aagtggtgaa tgtcacttct    240
ggcgagatag aaaatagaat gatgatgact ggtatgcaca ctgtggcaga catttctgc     300
gtctgttgtg ggtcaattgt tggatggaaa tatgagaccg cccatgagaa gagccaaaag    360
tacaaagaag gaaaatcagt gcttgagcgg tttaagatta ctggacctga tggaagccat    420
tactgggcta gtcatgatac tcatgttgca ggaagtgatg ctgatgatgt tgatcacca     480
ttcagaacaa aaattctatc caaaaatgta cattctttaa cccaccaccc tattagttct    540
ttatggacca ttggattctt gaatagctta agctctacaa cttctttaag cttgtcctct    600
attgtgtatg atgatatgga agcaccatgt gttgttgcaa actaacacga ccatctgcct    660
gtatttgttt gcaatgacaa gacattacta gtagcaacca ctctgctttc attgcttcga    720
aaaaaaaaaa aaaaaaaaaa a                                              741
```

<210> SEQ ID NO 14
<211> LENGTH: 129
<212> TYPE: PRT
<213> ORGANISM: Solanum tuberosum

<400> SEQUENCE: 14

```
Met Gly Arg Leu Phe Val Leu Thr Leu Glu Gly Lys Ile Tyr Ser Cys
1               5                   10                  15
```

Lys His Cys Gly Thr His Leu Ala Leu Ser Glu Asn Ile Val Ser Lys
        20                  25                  30

Ser Phe His Cys Lys His Gly Lys Ala Tyr Leu Phe Ser Lys Val Val
        35                  40                  45

Asn Val Thr Ser Gly Glu Ile Glu Asn Arg Met Met Met Thr Gly Met
50                  55                  60

His Thr Val Ala Asp Ile Phe Cys Val Cys Gly Ser Ile Val Gly
65                  70                  75                  80

Trp Lys Tyr Glu Thr Ala His Glu Lys Ser Gln Lys Tyr Lys Glu Gly
                85                  90                  95

Lys Ser Val Leu Glu Arg Phe Lys Ile Thr Gly Pro Asp Gly Ser His
            100                 105                 110

Tyr Trp Ala Ser His Asp Thr His Val Ala Gly Ser Asp Ala Asp Asp
        115                 120                 125

Val

<210> SEQ ID NO 15
<211> LENGTH: 1032
<212> TYPE: DNA
<213> ORGANISM: Zea mays
<220> FEATURE:
<221> NAME/KEY: misc_feature
<222> LOCATION: (242)..(249)
<223> OTHER INFORMATION: n is a, c, g, or t
<220> FEATURE:
<221> NAME/KEY: misc_feature
<222> LOCATION: (954)..(978)
<223> OTHER INFORMATION: n is a, c, g, or t

<400> SEQUENCE: 15
aagcgtgcag ctattcggtt atttaagagt gacgttggaa ccgaacacac aatacaatgc     60
agatttgtac atactgccct cgcttgacac ccaggtcgac cagacacttg agaaatttac    120
tttacttatt tggtcactag tgcttggcat acaactcaga tggacttata agcaacacag    180
gttacgcaca tatacagcgg taacatctaa tgacttccag aagcaatagg agggatatga    240
tnnnnnnnnc atgtcacctg gaacagcaac aatttacgcc ggcgaattat ttcaatggag    300
caatccccgg ctgtcggctg cctaaagagc aacgccaccc aggttattta caggggatca    360
acgacaggct tgagcttgtt ggatcgtgtt ttatatgtca tcggcgtcgc ttccgcccaa    420
gtgagcatct tgtggaaccc agtattggct tccgtcaggg cccgacacct tgtacctctc    480
cagaataaac ttgccttcct tgtatctctg gcccttctca tgtgccgcat catatttcca    540
cccaactatg gatccacagc caacacagaa gatatcagaa acagtatgca ttcctgtgat    600
catcatgcgg tcttctttta ctccagaagt cacgttgaca accttatgga agaggtacgc    660
cttgccgtgc ttgcactgga aggccttgga gatgatgtcg ctggcaacgc cgaggtgggt    720
cttgcagtgt ttgcagctgt agacgttgcc gtccaggtgc atcaggaaca ggcgccccat    780
cgccgccttc tctcccacct gccgcaactc cgctccaacc cctctctctc ggcttctcgt    840
caattccacc cagcgcacgg cgtcgagggc cactctagcc ccgatcgccg cggctcgaaa    900 tccctcttc cggcttcctc ggatcggaga ctgggagcgg gagttgttta ttgnnnnnnn    960
nnnnnnnnnn nnnnnnnngc ggcggtggta tctggtatgg tgcgaatgtg cgatgtgtca   1020
gcgagcgtcg tg                                                       1032

<210> SEQ ID NO 16
<211> LENGTH: 129
<212> TYPE: PRT

<213> ORGANISM: Zea mays

<400> SEQUENCE: 16

```
Met Gly Arg Leu Phe Leu Met His Leu Asp Gly Asn Val Tyr Ser Cys
1               5                   10                  15

Lys His Cys Lys Thr His Leu Gly Val Ala Ser Asp Ile Ile Ser Lys
            20                  25                  30

Ala Phe Gln Cys Lys His Gly Lys Ala Tyr Leu Phe His Lys Val Val
        35                  40                  45

Asn Val Thr Ser Gly Val Lys Glu Asp Arg Met Met Ile Thr Gly Met
    50                  55                  60

His Thr Val Ser Asp Ile Phe Cys Val Gly Cys Gly Ser Ile Val Gly
65                  70                  75                  80

Trp Lys Tyr Asp Ala Ala His Glu Lys Gly Gln Arg Tyr Lys Glu Gly
                85                  90                  95

Lys Phe Ile Leu Glu Arg Tyr Lys Val Ser Gly Pro Asp Gly Ser Gln
            100                 105                 110

Tyr Trp Val Pro Gln Asp Ala His Leu Gly Gly Ser Asp Ala Asp Asp
        115                 120                 125

Ile
```

<210> SEQ ID NO 17
<211> LENGTH: 920
<212> TYPE: DNA
<213> ORGANISM: Zea mays

<400> SEQUENCE: 17

```
gcacgagaac aaaccccgca cgactcgttc tcattccact ctccaacgcg caccgggcgg      60
tttttcgttc ctttcttttt ttttcccctc ttcccttcc ccttctcctt ccagcggcgc     120
tcaggccacc gccggccaat cccatcaccc gccggatagg gatcgacccg ttcgttgatt    180
ggcgcgcgcc tgcgatcgat cgattggatt gcagggttag ggcggccgcc gtcgagatag    240
atcgatccat ccatcgatcg aattggtttt gttggtggat cggagatatt cattcgggtc    300
catgggtcgg ctgctgctgg tgagcctccc ggcgacgggc gccgtcatct accgctgcaa    360
gcactgcgac acccacctcg cctacgacac cgacatcatc gcaaggacgt tccgctgcaa    420
gaacggcaag gcctacctct tcaacaggat cgtgaatgtg aatgttggta cgaaggagga    480
ggaccggatg atgacgacgg gcctgcacac cgtgtgcgac atcttctgcg tcgcctgcgg    540
agccatactc ggctggaaat acctcgtcgc cttcgacaag agccagaggt acaaggaagg    600
caagttcatc ctcgacaggt ccaccgcctt ggcagccgct cctggtgatg ccgctgctga    660
ccaccaccac caccacgctc gcgtagcaag ctccgatgac gaagatgacc atatgtgaat    720
gatgatgatg atgaatgtca tctgcattgc attcaccata tcccttgct atctgtaaat     780
actctactcc gcttgttgta gtcgttcgtc gtaaagcacc tatatgtttc catttgttca    840
acctatcaga ctatgatatg atcagcaagt aaggtccatt tgtttggatg cagcgacagt    900
tacaaacaaa aaaattaaaa                                                920
```

<210> SEQ ID NO 18
<211> LENGTH: 138
<212> TYPE: PRT
<213> ORGANISM: Zea mays

<400> SEQUENCE: 18

```
Met Gly Arg Leu Leu Leu Val Ser Leu Pro Ala Thr Gly Ala Val Ile
1               5                   10                  15
```

Tyr Arg Cys Lys His Cys Asp Thr His Leu Ala Tyr Asp Thr Asp Ile
            20                  25                  30

Ile Ala Arg Thr Phe Arg Cys Lys Asn Gly Lys Ala Tyr Leu Phe Asn
        35                  40                  45

Arg Ile Val Asn Val Asn Val Gly Thr Lys Glu Glu Asp Arg Met Met
    50                  55                  60

Thr Thr Gly Leu His Thr Val Cys Asp Ile Phe Cys Val Ala Cys Gly
65                  70                  75                  80

Ala Ile Leu Gly Trp Lys Tyr Leu Val Ala Phe Asp Lys Ser Gln Arg
                85                  90                  95

Tyr Lys Glu Gly Lys Phe Ile Leu Asp Arg Ser Thr Ala Leu Ala Ala
            100                 105                 110

Ala Pro Gly Asp Ala Ala Ala Asp His His His His Ala Arg Val
        115                 120                 125

Ala Ser Ser Asp Asp Glu Asp Asp His Met
    130                 135

<210> SEQ ID NO 19
<211> LENGTH: 360
<212> TYPE: DNA
<213> ORGANISM: Oryza sativa

<400> SEQUENCE: 19
atggggctgc tgttcgtgga gctgctcccg cggcacggcg acggggagg ccccgcgtcg       60 gcggtgctca gtgccgccg gtgccgcgtc gacgccgcct ccgccgacgc catcctctca      120
cgggacttcc gcggccgatt cggccgcgcc tacctcttcg accacgtggt gaatatatcc      180
ttagggccta atgaggatcg gtatctgatg accggactgc atacggtgaa agatatctac      240
tgtagctgtt gccagcaaat tctcggctgg agatatgaga agcatacga agagagcgag      300 aagtacaagg aaggcaagtt catcctggag aaggccagga tgtggaaaga agcccggtga      360

<210> SEQ ID NO 20
<211> LENGTH: 119
<212> TYPE: PRT
<213> ORGANISM: Oryza sativa

<400> SEQUENCE: 20

Met Gly Leu Leu Phe Val Glu Leu Leu Pro Arg His Gly Asp Gly Gly
1               5                   10                  15

Gly Pro Ala Ser Ala Val Leu Lys Cys Arg Arg Cys Arg Val Asp Ala
            20                  25                  30

Ala Ser Ala Asp Ala Ile Leu Ser Arg Asp Phe Arg Gly Arg Phe Gly
        35                  40                  45

Arg Ala Tyr Leu Phe Asp His Val Val Asn Ile Ser Leu Gly Pro Asn
    50                  55                  60

Glu Asp Arg Tyr Leu Met Thr Gly Leu His Thr Val Lys Asp Ile Tyr
65                  70                  75                  80

Cys Ser Cys Cys Gln Gln Ile Leu Gly Trp Arg Tyr Glu Lys Ala Tyr
                85                  90                  95

Glu Glu Ser Glu Lys Tyr Lys Glu Gly Lys Phe Ile Leu Glu Lys Ala
            100                 105                 110

Arg Met Trp Lys Glu Ala Arg
        115

<210> SEQ ID NO 21
<211> LENGTH: 836

<212> TYPE: DNA
<213> ORGANISM: Oryza sativa

<400> SEQUENCE: 21

```
gattttctt ctcccaaact ccggcgactc ctccgctaat ccctccggc gccgcctcct    60
ctccgctccc cgcgccccc acctccggtc acgcccgatc ggattggttg agttgcctcg    120
agggattttt gctctcgagg tatggtgttc atggcggagc tggtgggtcc gcgggtgtac   180
agctgctgca actgccggaa ccacgtctgc ctccacgacg acatcatctc caaggctttt   240
caggggagga atggccgtgc ctttctgttc tctcatgcca tgaatgttgt tgtgggcgcg   300
aaggaggaca ggcaacttat gacggggctt cacactgttg ctgatatcta ttgcaatgat   360
tgccgggagg tgttgggctg gaagtacgag agagcctatg aggaaacaca gaagtacaag   420
gaagggaagt tcatatttga gaagtcaaaa atcgtcaaag agaactggta gaatccaaaa   480
gattaggcac tccaaacttt ctttagagga tgaaacattc actgttccaa ggttatcagt   540
gtgttctggt tctttatgtc tttgtaaata tcagtcatcc acaagtttta atcttaagtc   600
tgcctgttct tgccttgccg tgaagtgtaa attgttcttg ctcccgtttc tttctgtgaa   660
taacatatgg cctgtgggta tttgttcttg aaccatgtgt gctaatgtgc gtaatttat    720
aggtactaaa agaatgtttg tatctttctc ctgcacaaga ataccgcgtg gagatttaca   780
gtcaaatata atctgacatg atttaatcaa aatttgttgg gaagttgtga agtaag       836
```

<210> SEQ ID NO 22
<211> LENGTH: 109
<212> TYPE: PRT
<213> ORGANISM: Oryza sativa

<400> SEQUENCE: 22

```
Met Val Phe Met Ala Glu Leu Val Gly Pro Arg Val Tyr Ser Cys Cys
1               5                   10                  15

Asn Cys Arg Asn His Val Cys Leu His Asp Asp Ile Ile Ser Lys Ala
            20                  25                  30

Phe Gln Gly Arg Asn Gly Arg Ala Phe Leu Phe Ser His Ala Met Asn
        35                  40                  45

Val Val Gly Ala Lys Glu Asp Arg Gln Leu Met Thr Gly Leu His
    50                  55                  60

Thr Val Ala Asp Ile Tyr Cys Asn Asp Cys Arg Glu Val Leu Gly Trp
65                  70                  75                  80

Lys Tyr Glu Arg Ala Tyr Glu Glu Thr Gln Lys Tyr Lys Glu Gly Lys
                85                  90                  95

Phe Ile Phe Glu Lys Ser Lys Ile Val Lys Glu Asn Trp
            100                 105
```

<210> SEQ ID NO 23
<211> LENGTH: 913
<212> TYPE: DNA
<213> ORGANISM: Oryza sativa

<400> SEQUENCE: 23

```
gctgcttttg cttcggtcac ccggtcagtg ctgcagacaa gccaccccct tcctcgcgta    60
gactgctccc cccacaaaca aaagcaatcc taatctcgga ttcgaggcga acgagcggcg   120
gcgagggagg gggactagcg gcgatcgcga ttggagtcgg gtggacaccg atcgcggcgg   180
cgctctgggg gatcggggtg tggaatcgag ggggaggggag gaggagacgg aggcgatggg   240
gcggctgttc gtgatgcacc tggaagggaa ggtgtacagc tgcaagcact gccacacgca   300
```

```
cctcggcctc tcctccgaca tcatctccaa gtccttccat tgcaagcacg ggaaggcgta     360
cctcttcaat aaggttgtca atgtgacttc tggagtaaaa gaggatcgca tgatgataac     420
cggaatgcat actgtgtctg atatcttctg tgttggctgc ggatccattg ttggatggaa     480
atatgaagct gcacatgaga agagccagag gtacaaggaa gggaaattta ttttagagag     540
gtataaggtg tctggtcctg atggcagcca ctactttgtt acacatgatg ctcatgttgg     600
gggaagcgac gtggacgacg tatgaagcac aactcgacat gctcaagcct atccatgta      660 atccatgtaa ataacccaag tgtttgttgg tcttagttac ccggggattt gcttccattc     720
agagcaaccc cagcgtaatt gttgtcctag atgacctaat atcctatcat cttccttcag     780
gagttcaggt tattattggg tgttaccgtc tgtatatgca tgtaaccagt gatgcctgta     840
gtagccccct aaaagctgtt gtaatcctgg aatgtatctc aggccctaat gactaaataa     900
aattctgctt ctc                                                        913
```

<210> SEQ ID NO 24
<211> LENGTH: 129
<212> TYPE: PRT
<213> ORGANISM: Oryza sativa

<400> SEQUENCE: 24

```
Met Gly Arg Leu Phe Val Met His Leu Glu Gly Lys Val Tyr Ser Cys
1               5                   10                  15

Lys His Cys His Thr His Leu Gly Leu Ser Ser Asp Ile Ile Ser Lys
            20                  25                  30

Ser Phe His Cys Lys His Gly Lys Ala Tyr Leu Phe Asn Lys Val Val
        35                  40                  45

Asn Val Thr Ser Gly Val Lys Glu Asp Arg Met Met Ile Thr Gly Met
    50                  55                  60

His Thr Val Ser Asp Ile Phe Cys Val Gly Cys Gly Ser Ile Val Gly
65                  70                  75                  80

Trp Lys Tyr Glu Ala Ala His Glu Lys Ser Gln Arg Tyr Lys Glu Gly
                85                  90                  95

Lys Phe Ile Leu Glu Arg Tyr Lys Val Ser Gly Pro Asp Gly Ser His
            100                 105                 110

Tyr Phe Val Thr His Asp Ala His Val Gly Gly Ser Asp Val Asp Asp
        115                 120                 125

Val
```

<210> SEQ ID NO 25
<211> LENGTH: 2193
<212> TYPE: DNA
<213> ORGANISM: Oryza sativa

<400> SEQUENCE: 25

```
aatccgaaaa gtttctgcac cgttttcacc ccctaactaa caatataggg aacgtgtgct      60
aaatataaaa tgagacctta tatgtgtagc gctgataact agaactatgc aagaaaaact     120
catccaccta ctttagtggc aatcgggcta aataaaaag agtcgctaca ctagtttcgt      180
tttccttagt aattaagtgg gaaaatgaaa tcattattgc ttagaatata cgttcacatc     240
tctgtcatga agttaaatta ttcgaggtag ccataattgt catcaaactc ttcttgaata     300
aaaaaatctt tctagctgaa ctcaatgggt aaagagagag atttttttta aaaaataga     360 atgaagatat tctgaacgta ttggcaaaga tttaaacata taattatata attttatagt     420
ttgtgcattc gtcatatcgc acatcattaa ggacatgtct tactccatcc caatttttat     480
```

-continued

```
ttagtaatta aagacaattg acttatttt attatttatc tttttcgat tagatgcaag    540 gtacttacgc acacactttg tgctcatgtg catgtgtgag tgcacctcct caatacacgt   600
tcaactagca acacatctct aatatcactc gcctatttaa tacatttagg tagcaatatc   660
tgaattcaag cactccacca tcaccagacc acttttaata atatctaaaa tacaaaaaat   720
aattttacag aatagcatga aaagtatgaa acgaactatt taggttttc acatacaaaa    780 aaaaaaagaa ttttgctcgt gcgcgagcgc caatctccca tattgggcac acaggcaaca   840
acagagtggc tgcccacaga acaacccaca aaaaacgatg atctaacgga ggacagcaag   900
tccgcaacaa cctttaaca gcaggctttg cggccaggag agaggaggag aggcaaagaa    960
aaccaagcat cctcctcctc ccatctataa attcctcccc cctttcccc tctctatata    1020 ggaggcatcc aagccaagaa gagggagagc accaaggaca cgcgactagc agaagccgag   1080
cgaccgcctt cttcgatcca tatcttccgg tcgagttctt ggtcgatctc ttccctcctc   1140
cacctcctcc tcacagggta tgtgccctc ggttgttctt ggatttattg ttctaggttg    1200
tgtagtacgg gcgttgatgt taggaaaggg gatctgtatc tgtgatgatt cctgttcttg   1260
gatttgggat agaggggttc ttgatgttgc atgttatcgg ttcggtttga ttagtagtat   1320
ggttttcaat cgtctggaga gctctatgga aatgaaatgg tttagggtac ggaatcttgc   1380
gattttgtga gtacctttg tttgaggtaa aatcagagca ccggtgattt tgcttggtgt    1440
aataaaagta cggttgtttg gtcctcgatt ctggtagtga tgcttctcga tttgacgaag   1500
ctatcctttg tttattccct attgaacaaa aataatccaa ctttgaagac ggtcccgttg   1560
atgagattga atgattgatt cttaagcctg tccaaaattt cgcagctggc ttgtttagat   1620
acagtagtcc ccatcacgaa attcatggaa acagttataa tcctcaggaa caggggattc   1680
cctgttcttc cgatttgctt tagtcccaga attttttc ccaaatatct taaaaagtca     1740
ctttctggtt cagttcaatg aattgattgc tacaaataat gcttttatag cgttatccta   1800
gctgtagttc agttaatagg taatacccct atagttagt caggagaaga acttatccga    1860
tttctgatct ccattttaa ttatatgaaa tgaactgtag cataagcagt attcatttgg    1920 attattttt ttattagctc tcaccccttc attattctga gctgaaagtc tggcatgaac    1980
tgtcctcaat tttgttttca aattcacatc gattatctat gcattatcct cttgtatcta   2040
cctgtagaag tttctttttg gttattcctt gactgcttga ttacagaaag aaatttatga   2100
agctgtaatc gggatagtta tactgcttgt tcttatgatt catttccttt gtgcagttct   2160
tggtgtagct tgccactttc accagcaaag ttc                                2193
```

<210> SEQ ID NO 26
<211> LENGTH: 59
<212> TYPE: DNA
<213> ORGANISM: Artificial sequence
<220> FEATURE:
<223> OTHER INFORMATION: forward primer prm03198

<400> SEQUENCE: 26
ggggacaagt ttgtacaaaa aagcaggctt cacaatgggt agggttttta tggttgatc    59

<210> SEQ ID NO 27
<211> LENGTH: 55
<212> TYPE: DNA
<213> ORGANISM: Artificial sequence
<220> FEATURE:
<223> OTHER INFORMATION: reverse primer prm03199

<400> SEQUENCE: 27

```
ggggaccact tgtacaaga aagctgggta atcaagcatc atctccatca ctaac        55

<210> SEQ ID NO 28
<211> LENGTH: 52
<212> TYPE: DNA
<213> ORGANISM: Artificial sequence
<220> FEATURE:
<223> OTHER INFORMATION: Primer prm03196

<400> SEQUENCE: 28
ggggacaagt tgtacaaaa aagcaggctt cacaatggct gtcggagatg at           52

<210> SEQ ID NO 29
<211> LENGTH: 6
<212> TYPE: PRT
<213> ORGANISM: Unknown
<220> FEATURE:
<223> OTHER INFORMATION: Motif of the YIPPEE-like polypeptide

<400> SEQUENCE: 29

Lys Tyr Lys Glu Gly Lys
1               5

<210> SEQ ID NO 30
<211> LENGTH: 6
<212> TYPE: PRT
<213> ORGANISM: Unknown
<220> FEATURE:
<223> OTHER INFORMATION: Motif of the YIPPEE-like polypeptide

<400> SEQUENCE: 30

Gly Arg Ala Tyr Leu Phe
1               5
```

PLANTS HAVING IMPROVED GROWTH CHARACTERISTICS AND METHOD FOR MAKING THE SAME

RELATED APPLICATIONS

This application is a national stage application (under 35 U.S.C. 371) of PCT/EP2005/053324 filed Jul. 12, 2005, which claims benefit of European application 04103303.6 filed Jul. 12, 2004 and U.S. Provisional application 60/588,917 filed Jul. 16, 2004.

SEQUENCE LISTING SUBMISSION

The Sequence Listing associated with this application is filed in electronic format via EFS-Web and hereby incorporated by reference into the specification in its entirety. The name of the text file containing the Sequence Listing is Sequence_Listing_14546_00009_US. The size of the text file is 31 KB, and the text file was created on Aug. 13, 2009.

The present invention relates generally to the field of molecular biology and concerns a method for improving plant growth characteristics. More specifically, the present invention concerns a method for improving plant growth characteristics, in particular yield, by increasing activity in a plant of a YIPPEE-like polypeptide or a homologue thereof. The present invention also concerns plants having increased activity of a YIPPEE-like polypeptide or a homologue thereof, which plants have improved growth characteristics relative to corresponding wild type plants. The invention also provides constructs useful in the methods of the invention.

The ever-increasing world population and the dwindling supply of arable land available for agriculture fuel agricultural research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits. A trait of particular economic interest is yield. Yield is normally defined as the measurable produce of economic value from a crop. This may be defined in terms of quantity and/or quality. Yield is directly dependent on several factors, for example, the number and size of the organs, plant architecture (for example, the number of branches), seed production and more. Root development, nutrient uptake and stress tolerance may also be important factors in determining yield. Crop yield may therefore be increased by optimizing one of the abovementioned factors.

The ability to improve various growth characteristics of a plant would have many applications in areas such as crop enhancement, plant breeding, in the production of ornamental plants, aboriculture, horticulture and forestry. Improving growth characteristics, such as yield may also find use in the production of algae for use in bioreactors (for the biotechnological production of substances such as pharmaceuticals, antibodies, or vaccines, or for the bioconversion of organic waste) and other such areas.

It has now been found that increasing activity in a plant of a YIPPEE-like polypeptide gives plants having improved growth characteristics relative to corresponding wild type plants.

The YIPPEE gene was first identified in *Drosophila* and revealed a novel family of putative zinc binding proteins highly conserved among eukaryotes (Roxstrom-Lindquist K. and Faye I. (2001) Insect Mol Biol. 10(1): 77-86). The YIPPEE protein was characterized and was found to contain a putative zinc-finger-like metal binding domain. It was the first characterized member of a conserved gene family of proteins present in diverse eukaryotic organisms, ranging from cellular slime mould to humans. The YIPPEE gene is ubiquitously expressed in different developmental stages of *Drosophila*. The high degree of YIPPEE-like sequence conservation between a wide range of species is an indication that the YIPPEE protein is of general importance in eukaryotes.

According to the present invention, there is provided a method for improving the growth characteristics of a plant, comprising increasing activity in a plant of a YIPPEE-like polypeptide or a homologue thereof.

Advantageously, performance of the methods according to the present invention results in plants having a variety of improved growth characteristics, especially increased yield, particularly seed yield.

The term "increased yield" as defined herein is taken to mean an increase in any one or more of the following, each relative to corresponding wild type plants: (i) increased biomass (weight) of one or more parts of a plant, particularly aboveground (harvestable) parts, increased root biomass or increased biomass of any other harvestable part; (ii) increased seed yield, which includes an increase in seed biomass (seed weight) and which may be an increase in the seed weight per plant or on an individual seed basis; (iii) increased number of (filled) seeds; (iv) increased seed size, which may also influence the composition of seeds; (v) increased seed volume, which may also influence the composition of seeds; (vi) increased harvest index, which is expressed as a ratio of the yield of harvestable parts, such as seeds, over the total biomass; and (vii) increased thousand kernel weight (TKW), which is extrapolated from the number of filled seeds counted and their total weight. An increased TKW may result from an increased seed size and/or seed weight.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, among others. Taking rice as an example, a yield increase may be manifested by an increase in one or more of the following: number of plants per hectare or acre, number of panicles per plant, number of spikelets per panicle, number of flowers per panicle, increase in the seed filling rate, increase in thousand kernel weight, among others. An increase in yield may also result in modified architecture, or may occur as a result of modified architecture.

According to a preferred feature, performance of the methods of the invention result in plants having increased yield, particularly seed yield. Therefore, according to the present invention, there is provided a method for increasing plant yield, particularly seed yield, which method comprises increasing activity in a plant of a YIPPEE-like polypeptide or a homologue thereof.

Since the transgenic plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant (including seeds), or may be throughout substantially the whole plant. A plant having an increased growth rate may even exhibit early flowering. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible. If the growth rate is sufficiently increased, it may allow for the sowing of further seeds of the same plant species (for example sowing and harvesting of rice plants followed by sowing and harvesting of further rice plants all within one conventional growing period). Similarly, if the growth rate is sufficiently increased, it may allow for the sowing of further seeds of different plants species (for example the sowing and harvesting of rice plants followed by, for example, the sowing and optional harvesting of soy bean, potato or any other suitable plant). Harvesting additional times from the same rootstock in the case of some plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

Performance of the methods of the invention gives plants having an increased growth rate. Therefore, according to the present invention, there is provided a method for increasing the growth rate of plants, which method comprises increasing activity in a plant of a YIPPEE-like polypeptide or a homologue thereof.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the typical stresses to which a plant may be exposed. These stresses may be the everyday biotic and/or abiotic (environmental) stresses to which a plant is exposed. Typical abiotic or environmental stresses include temperature stresses caused by atypical hot or cold/freezing temperatures; salt stress; water stress (drought or excess water). Abiotic stresses may also be caused by chemicals. Biotic stresses are typically those stresses caused by pathogens, such as bacteria, viruses, fungi and insects.

The abovementioned growth characteristics may advantageously be modified in any plant.

The term "plant" as used herein encompasses whole plants, ancestors and progeny of the plants and plant parts, including seeds, shoots, stems, leaves, roots, flowers (including tubers), and tissues and organs, wherein each of the aforementioned comprise the gene/nucleic acid of interest and/or a genetic modification, preferably in the locus of a YIPPEE-like gene. The term "plant" also encompasses suspension cultures, callus tissue, embryos, meristematic regions, gametophytes, sporophytes, pollen, and microspores, again wherein each of the aforementioned comprise the gene/nucleic acid of interest and/or a genetic modification, preferably in the locus of a YIPPEE-like gene.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising Acacia spp., Acer spp., Actinidia spp., Aesculus spp., Agathis australis, Albizia amara, Alsophila tricolor, Andropogon spp., Arachis spp, Areca catechu, Astelia fragrans, Astragalus cicer, Baikiaea plurijuga, Betula spp., Brassica spp., Bruguiera gymnorrhiza, Burkea africana, Butea frondosa, Cadaba farinosa, Calliandra spp, Camellia sinensis, Canna indica, Capsicum spp., Cassia spp, Centroema pubescens, Chaenomeles spp., Cinnamomum cassia, Coffea arabica, Colophospermum mopane, Coronillia varia, Cotoneaster serotina, Crataegus spp., Cucumis spp., Cupressus spp., Cyathea dealbata, Cydonia oblonga, Cryptomeria japonica, Cymbopogon spp., Cynthea dealbata, Cydonia oblonga, Dalbergia monetaria, Davallia divaricata, Desmodium spp., Dicksonia squarosa, Diheteropogon amplectens, Dioclea spp, Dolichos spp., Dorycnium rectum, Echinochloa pyramidalis, Ehrartia spp., Eleusine coracana, Eragrestis spp., Erythrina spp., Eucalyptus spp., Euclea schimperi, Eulalia villosa, Fagopyrum spp., Feijoa sellowiana, Fragaria spp., Flemingia spp, Freycinetia banksii, Geranium thunbergii, Ginkgo biloba, Glycine javanica, Gliricidia spp, Gossypium hirsutum, Grevillea spp., Guibourtia coleospemma, Hedysarum spp., Hemarthia altissima, Heteropogon contortus, Hordeum vulgare, Hyparrhenia rufa, Hypencum erectum, Hyperthelia dissoluta, Indigo incamata, Iris spp., Leptarrheria pyrolifolia, Lespediza spp., Lettuca spp., Leucaena leucocephala, Loudetia simplex, Lotonus bainesii, Lotus spp., Macrotyloma axillare, Malus spp., Manihot esculenta, Medicago sativa, Metasequoia glyptostroboides, Musa sapientum, Nicotianum spp., Onobrychis spp., Ornithopus spp., Oryza spp., Peltophorum africanum, Pennisetum spp., Persea gratissima, Petunia spp., Phaseolus spp., Phoenix canariensis, Phormium cookianum, Photinia spp., Picea glauca, Pinus spp., Pisum sativum, Podocarpus totara, Pogonarthria fleckii, Pogonarthria squarrosa, Populus spp., Prosopis cineraria, Pseudotsuga menziesii, Pterolobium stellatum, Pyrus communis, Quercus spp., Rhaphiolepsis umbellata, Rhopalostylis sapida, Rhus natalensis, Ribes grossularia, Ribes spp., Robinia pseudoacacia, Rosa spp., Rubus spp., Salix spp., Schyzachyrium sanguineum, Sciadopitys verticillata, Sequoia sempervirens, Sequoiadendron giganteum, Sorghum bicolor, Spinacia spp., Sporobolus fimbriatus, Stiburus alopecuroides, Stylosanthos humills, Tadehagi spp, Taxodium distichum, Themeda triandra, Trifolium spp., Triticum spp., Tsuga heterophylla, Vaccinium spp., Vicia spp., Vitis vinifera, Watsonia pyramidata, Zantedeschia aethiopica, Zea mays, amaranth, artichoke, asparagus, broccoli, Brussel sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant such as soybean, sunflower, canola, alfalfa, rapeseed, cotton, tomato, potato or tobacco. Further preferably, the plant is a monocotyledonous plant, such as sugar cane. More preferably the plant is a cereal, such as rice, maize, wheat, barley, millet, rye, sorghum or oats.

The activity of a YIPPEE-like polypeptide may be increased by increasing levels in a plant of the polypeptide. Alternatively, activity may also be increased when there is no change in levels of a YIPPEE-like polypeptide, or even when there is a reduction in levels of a YIPPEE-like polypeptide. This may occur when the intrinsic properties of the polypeptide are altered, for example, by making mutant versions that are more active that the wild type polypeptide.

The term "YIPPEE-like polypeptide or a homologue thereof" as defined herein refers to a polypeptide comprising: (i) a putative zinc-binding motif: 2xCXXC, where X is any amino acid residue; and (ii) the motif KYKEGK (SEQ ID NO: 29), allowing for one amino acid substitution at any position and any conservative amino acid substitution; and (iii) the motif GRAYLF (SEQ ID NO: 30), allowing for one amino acid substitution at any position and any conservative amino acid substitution. The putative zinc-binding motif: 2xCXXC is typically found with a gap of about 52 amino acids residues between the first and second CXXC, i.e. CXXC{52 amino acids}CXXC. The term "any conservative amino acid substitution" means that any one or more of the amino acid residues may be replaced with a conservative substitution. Conservative substitution tables are readily available in the art. The table below gives examples of conserved amino acid substitutions.

TABLE 1

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

A "YIPPEE-like polypeptide or a homologue thereof" may readily be identified using routine techniques well known in the art. The motifs defined above are highly conserved, thereby allowing a person skilled in the art to readily identify other YIPPEE-like sequences based on the presence of these motifs.

The plant YIPPEE-like polypeptide sequence represented by SEQ ID NO: 2, encoded by the nucleic acid of SEQ ID NO: 1, was found on the basis of homology to a transcription factor in *Drosophila*. Examples of plant-derived polypeptides falling under the definition of a "YIPPEE-like polypeptide or a homologue thereof" include: At3g08990 (SEQ ID NO: 4), At3g11230 (SEQ ID NO: 6), At2g40110 (SEQ ID NO: 8), At4g27740 (SEQ ID NO: 10) and At5g53940 (SEQ ID NO: 12), all from *Arabidopsis thaliana*; AB061267 (SEQ ID NO: 14), from potato; AY109711.1 (SEQ ID NO: 16) and AY104347.1 (SEQ ID NO: 18) protein predictions in maize; NM_196100.1 (SEQ ID NO: 20), AK121352.1 (SEQ ID NO: 22) and AK109500.1 (SEQ ID NO: 24), protein predictions in rice. The table below shows the percentage homology of the aforementioned YIPPEE-like polypeptide sequences with SEQ ID NO: 2 based on overall global sequence alignment. Accession numbers 1 to 7 in the table refer to the protein and the remaining accession numbers refer to the mRNA with the corresponding SEQ ID NO giving the protein prediction. The percentage identity was calculated using an NCBI Align program with default parameters.

TABLE 2

Homology of YIPPEE-like protein sequences with SEQ ID NO: 2 based on overall global sequence alignment

| | Accession Number | SEQ ID NO | % Identity (Blast Align) | Source |
|---|---|---|---|---|
| 1 | At3G55890 (CDS1522) | SEQ ID NO: 2 | | *Arabidopsis thaliana* |
| 2 | At3g08990 | SEQ ID NO: 4 | 61 | *Arabidopsis thaliana* |
| 3 | At3g11230 | SEQ ID NO: 6 | 62 | *Arabidopsis thaliana* |
| 4 | At2g40110 | SEQ ID NO: 8 | 66 | *Arabidopsis thaliana* |
| 5 | At4g27740 | SEQ ID NO: 10 | 53 | *Arabidopsis thaliana* |
| 6 | At5g53940 | SEQ ID NO: 12 | 60 | *Arabidopsis thaliana* |
| 7 | AB061267 | SEQ ID NO: 14 | 63 | Potato |
| 8 | AY109711.1 | SEQ ID NO: 16 | 63 | Maize |
| 9 | AY104347.1 | SEQ ID NO: 18 | 60 | Maize |
| 10 | NM_196100.1 | SEQ ID NO: 20 | 50 | Rice |
| 11 | AK121352.1 | SEQ ID NO: 22 | 53 | Rice |
| 12 | AK109500.1 | SEQ ID NO: 24 | 64 | Rice |

It is to be understood that sequences falling under the definition of "YIPPEE-like polypeptide or homologue thereof" are not to be limited to the sequences represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22 and SEQ ID NO: 24, but that any polypeptide meeting the criteria of comprising: (i) a putative zinc-binding motif: 2xCXXC, where X is any amino acid residue; and (ii) the motif KYKEGK (SEQ ID NO: 29), allowing for one amino acid substitution at any position and any conservative amino acid substitution; and (iii) the motif GRAYLF (SEQ ID NO: 30), allowing for one amino acid substitution at any position and any conservative amino acid substitution may be suitable for use in the methods of the invention. The methods of the invention may also be performed when the polypeptide has at least one of the aforementioned motifs (i) to (iii).

The nucleic acid encoding a YIPPEE-like polypeptide or a homologue thereof may be any natural or synthetic nucleic acid. A YIPPEE-like polypeptide or a homologue thereof as defined hereinabove is one that is encoded by a YIPPEE-like nucleic acid/gene. Therefore the term "YIPPEE-like nucleic acid/gene" as defined herein is any nucleic acid/gene encoding a YIPPEE-like polypeptide or a homologue thereof as defined hereinabove. Examples of Yippee-like nucleic acids include those represented by any one of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 and SEQ ID NO: 23. YIPPEE-like nucleic acids/genes and variants thereof may be suitable in practising the methods of the invention. Variant YIPPEE-like nucleic acid/genes include portions of a YIPPEE-like nucleic acid/gene and/or nucleic acids capable of hybridising with a YIPPEE-like nucleic acid/gene.

The term portion as defined herein refers to a piece of DNA comprising at least 249 nucleotides and which portion encodes a polypeptide comprising any one or more of, and preferably all of: (i) a putative zinc-binding motif: 2xCXXC, where X is any amino acid residue; (ii) the motif KYKEGK (SEQ ID NO: 29), allowing for one amino acid substitution at any position and any conservative amino acid substitution; (iii) the motif GRAYLF (SEQ ID NO: 30), allowing for one amino acid substitution at any position and any conservative amino acid substitution. A portion may be prepared, for example, by making one or more deletions to a YIPPEE-like nucleic acid. The portions may be used in isolated form or they may be fused to other coding (or non coding) sequences in order to, for example, produce a protein that combines several activities. When fused to other coding sequences, the resulting polypeptide produced upon translation could be bigger than that predicted for the YIPPEE-like fragment. Preferably, the functional portion is a portion of a nucleic acid as represented by any one of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 and SEQ ID NO: 23.

Another variant YIPPEE-like nucleic acid/gene is a nucleic acid capable of hybridising under reduced stringency conditions, preferably under stringent conditions, with a YIPPEE-like nucleic acid/gene as hereinbefore defined, which hybridising sequence encodes a polypeptide comprising any one or more of, and preferably all of: (i) a putative zinc-binding motif: 2xCXXC, where X is any amino acid residue; (ii) the motif KYKEGK (SEQ ID NO: 29), allowing for one amino acid substitution at any position and any conservative amino acid substitution; (iii) the motif GRAYLF (SEQ ID NO: 30), allowing for one amino acid substitution at any position and any conservative amino acid substitution. Preferably, the hybridising sequence is one that is capable of hybridising to a nucleic acid as represented by any one of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 and SEQ ID NO: 23 or to a portion of any of the aforementioned sequences as defined hereinabove.

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration, ionic strength and hybridisation buffer composition.

"Stringent hybridisation conditions" and "stringent hybridisation wash conditions" in the context of nucleic acid hybridisation experiments such as Southern and Northern hybridisations are sequence dependent and are different under different environmental parameters. The skilled artisan is aware of various parameters which may be altered during hybridisation and washing and which will either maintain or change the stringency conditions.

The $T_m$ is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M. Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$ decreases about 1° C. per % base mismatch. The $T_m$ may be calculated using the following equations, depending on the types of hybrids:

1. DNA-DNA hybrids (Meinkoth and Wahl, Anal. Biochem., 138: 267-284, 1984):

$$T_m = 81.5° C. + 16.6 \times \log [Na^+]^a + 0.41 \times \%[G/C^b] - 500 \times [L^c]^{-1} - 0.61 \times \% \text{ formamide}$$

2. DNA-RNA or RNA-RNA hybrids:

$$T_m = 79.8 + 18.5 (\log_{10}[Na^+]^a) + 0.58 (\% G/C^b) + 11.8 (\% G/C^b)^2 - 820/L^c$$

3. oligo-DNA or oligo-RNA$^d$ hybrids:
   For <20 nucleotides: $T_m = 2(l_n)$
   For 20-35 nucleotides: $T_m = 22 + 1.46(l_n)$ $^a$ or for other monovalent cation, but only accurate in the 0.01-0.4 M range.
$^b$ only accurate for % GC in the 30% to 75% range.
$^c$ L=length of duplex in base pairs.
$^d$ Oligo, oligonucleotide; $l_n$, effective length of primer=2×(no. of G/C)+(no. of A/T).

Note: for each 1% formamide, the $T_m$ is reduced by about 0.6 to 0.7° C., while the presence of 6 M urea reduces the $T_m$ by about 30° C.

Specificity of hybridisation is typically the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. Generally, suitable stringent conditions for nucleic acid hybridisation assays or gene amplification detection procedures are as set forth above. Conditions of greater or less stringency may also be selected. Generally, low stringency conditions are selected to be about 50° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. For example, stringent conditions are those that are at least as stringent as, for example, conditions A-L; and reduced stringency conditions are at least as stringent as, for example, conditions M-R. Non-specific binding may be controlled using any one of a number of known techniques such as, for example, blocking the membrane with protein containing solutions, additions of heterologous RNA, DNA, and SDS to the hybridisation buffer, and treatment with Rnase. Examples of hybridisation and wash conditions are listed in Table 2 below.

region, which includes the gene of interest and 10 KB up- or down stream of the coding region.

The genetic modification may be introduced, for example, by any one (or more) of the following methods: TDNA acti-

TABLE 3

Examples of hybridisation and wash conditions

| Stringency Condition | Polynucleotide Hybrid± | Hybrid Length (bp)‡ | Hybridization Temperature and Buffer† | Wash Temperature and Buffer† |
|---|---|---|---|---|
| A | DNA:DNA | > or equal to 50 | 65° C. 1 × SSC; or 42° C., 1 × SSC and 50% formamide | 65° C.; 0.3 × SSC |
| B | DNA:DNA | <50 | Tb*; 1 × SSC | Tb*; 1 × SSC |
| C | DNA:RNA | > or equal to 50 | 67° C. 1 × SSC; or 45° C., 1 × SSC and 50% formamide | 67° C.; 0.3 × SSC |
| D | DNA:RNA | <50 | Td*; 1 × SSC | Td*; 1 × SSC |
| E | RNA:RNA | > or equal to 50 | 70° C. 1 × SSC; or 50° C., 1 × SSC and 50% formamide | 70° C.; 0.3 × SSC |
| F | RNA:RNA | <50 | Tf*; 1 × SSC | Tf*; 1 × SSC |
| G | DNA:DNA | > or equal to 50 | 65° C. 4 × SSC; or 45° C., 4 × SSC and 50% formamide | 65° C.; 1 × SSC |
| H | DNA:DNA | <50 | Th*; 4 × SSC | Th*; 4 × SSC |
| I | DNA:RNA | > or equal to 50 | 67° C. 4 × SSC; or 45° C., 4 × SSC and 50% formamide | 67° C.; 1 × SSC |
| J | DNA:RNA | <50 | Tj*; 4 × SSC | Tj*; 4 × SSC |
| K | RNA:RNA | > or equal to 50 | 70° C. 4 × SSC; or 40° C., 6 × SSC and 50% formamide | 67° C.; 1 × SSC |
| L | RNA:RNA | <50 | Tl*; 2 × SSC | Tl*; 2 × SSC |
| M | DNA:DNA | > or equal to 50 | 50° C. 4 × SSC; or 40° C., 6 × SSC and 50% formamide | 50° C.; 2 × SSC |
| N | DNA:DNA | <50 | Tn*; 6xSSC | Tn*; 6 × SSC |
| O | DNA:RNA | > or equal to 50 | 55° C. 4 × SSC; or 42° C., 6 × SSC and 50% formamide | 55° C.; 2 × SSC |
| P | DNA:RNA | <50 | Tp*; 6xSSC | Tp*; 6 × SSC |
| Q | RNA:RNA | > or equal to 50 | 60° C. 4 × SSC; or 45° C., 6 × SSC and 50% formamide | 60° C.; 2 × SSC |
| R | RNA:RNA | <50 | Tr*; 4 × SSC | Tr*; 4 × SSC |

‡The "hybrid length" is the anticipated length for the hybridising nucleic acid. When nucleic acids of known sequence are hybridised, the hybrid length may be determined by aligning the sequences and identifying the conserved regions described herein.
†SSPE (1 × SSPE is 0.15M NaCl, 10 mM NaH$_2$PO$_4$, and 1.25 mM EDTA, pH7.4) may be substituted for SSC (1 × SSC is 0.15M NaCl and 15 mM sodium citrate) in the hybridisation and wash buffers; washes are performed for 15 minutes after hybridisation is complete. The hybridisations and washes may additionally include 5 × Denhardt's reagent, .5-1.0% SDS, 100 µg/ml denatured, fragmented salmon sperm DNA, 0.5% sodium pyrophosphate, and up to 50% formamide.
*Tb-Tr: The hybridisation temperature for hybrids anticipated to be less than 50 base pairs in length should be 5-10° C. less than the melting temperature $T_m$ of the hybrids; the $T_m$ is determined according to the above-mentioned equations.
±The present invention also encompasses the substitution of any one, or more DNA or RNA hybrid partners with either a PNA, or a modified nucleic acid.

For the purposes of defining the level of stringency, reference can be made to Sambrook et al. (2001) Molecular Cloning: a laboratory manual, $3^{rd}$ Edition Cold Spring Harbor Laboratory Press, CSH, New York or to Current Protocols in Molecular Biology, John Wiley & Sons, N.Y. (1989).

The YIPPEE-like nucleic acid or variant thereof may be derived from any natural or artificial source. The nucleic acid/gene or variant thereof may be isolated from a microbial source, such as bacteria, yeast or fungi, or from a plant, algae or animal (including human) source. This nucleic acid may be modified from its native form in composition and/or genomic environment through deliberate human manipulation. The nucleic acid is preferably of plant origin, whether from the same plant species (for example to the one in which it is to be introduced) or whether from a different plant species. The nucleic acid may be isolated from a dicotyledonous species, preferably from the family Brassicaceae, further preferably from *Arabidopsis thaliana*. More preferably, the Yippee-like nucleic acid isolated from *Arabidopsis thaliana* is represented by SEQ ID NO: 1 and the YIPPEE-like amino acid sequence is as represented by SEQ ID NO: 2.

The activity of a YIPPEE-like polypeptide or a homologue thereof may be increased by introducing a genetic modification (preferably in the locus of a YIPPEE-like gene). The locus of a gene as defined herein is taken to mean a genomic vation, TILLING, site-directed mutagenesis, directed evolution, homologous recombination or by introducing and expressing in a plant a nucleic acid encoding a YIPPEE-like polypeptide or a homologue thereof. Following introduction of the genetic modification, there follows a step of selecting for increased activity of a YIPPEE-like polypeptide, which increase in activity gives plants having improved growth characteristics.

T-DNA activation tagging (Hayashi et al. Science (1992) 1350-1353) involves insertion of T-DNA usually containing a promoter (may also be a translation enhancer or an intron), in the genomic region of the gene of interest or 10 KB up- or down stream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near to the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of a YIPPEE-like gene using the technique of TILLING (Targeted Induced Local Lesions IN Genomes). This is a mutagenesis technology useful to generate and/or identify, and to eventually isolate mutagenised variants of a YIPPEE-like nucleic acid capable of exhibiting YIPPEE-like activity. TILLING also allows selection of plants carrying such mutant variants. These mutant variants may even exhibit higher YIPPEE-like activity than that exhibited by the gene in its natural form. TILLING combines high-density mutagenesis with high-throughput screening methods. The steps typically followed in TILLING are: (a) EMS mutagenesis (Redei and Koncz, 1992; Feldmann et al., 1994; Lightner and Caspar, 1998); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum Nat Biotechnol. 2000 April; 18(4):455-7, reviewed by Stemple 2004 (TILLING-a high-throughput harvest for functional genomics. Nat Rev Genet. 2004 February; 5(2):145-50.)).

Site directed mutagenesis may be used to generate variants of YIPPEE-like nucleic acids or portions thereof. Several methods are available to achieve site directed mutagenesis, the most common being PCR based methods (current protocols in molecular biology. Wiley Eds.).

Directed evolution may also be used to generate variants of YIPPEE-like nucleic acids. This consists of iterations of DNA shuffling followed by appropriate screening and/or selection to generate variants of YIPPEE-like nucleic acids or portions thereof encoding polypeptides having a modified biological activity (Castle et al., (2004) Science 304(5674): 11514; U.S. Pat. Nos. 5,811,238 and 6,395,547).

TDNA activation, TILLING, directed evolution and site-directed mutagenesis are examples of technologies that enable the generation of novel alleles and YIPPEE-like variants.

Homologous recombination allows introduction in a genome of a selected nucleic acid at a defined selected position. Homologous recombination is a standard technology used routinely in biological sciences for lower organisms such as yeast or the moss *physcomitrella*. Methods for performing homologous recombination in plants have been described not only for model plants (Offring a et al., Extrachromosomal homologous recombination and gene targeting in plant cells after *Agrobacterium*-mediated transformation. 1990 EMBO J. 1990 Oct; 9(10):3077-84) but also for crop plants, for example rice (Terada R, Urawa H, Inagaki Y, Tsugane K, Iida S. Efficient gene targeting by homologous recombination in rice. Nat Biotechnol. 2002. Iida and Terada: A tale of two integrations, transgene and T-DNA: gene targeting by homologous recombination in rice. Curr Opin Biotechnol. 2004 Apr; 15(2):132-8). The nucleic acid to be targeted (which may be a YIPPEE-like nucleic acid or variant thereof as hereinbefore defined) need not be targeted to the locus of a YIPPEE-like gene, but may be introduced in, for example, regions of high expression. The nucleic acid to be targeted may be an improved allele used to replace the endogenous gene or may be introduced in addition to the endogenous gene.

According to a preferred embodiment of the invention, plant growth characteristics may be improved by introducing and expressing in a plant a nucleic acid encoding a YIPPEE-like polypeptide or a homologue thereof.

A preferred method for introducing a genetic modification (which in this case need not be in the locus of an YIPPEE-like gene) is to introduce and express in a plant a nucleic acid encoding a YIPPEE-like polypeptide or a homologue thereof An YIPPEE-like polypeptide or a homologue thereof as mentioned above is one comprising (i) a putative zinc-binding motif: 2xCXXC, where X is any amino acid residue; and (ii) the motif KYKEGK (SEQ ID NO: 29), allowing for one amino acid substitution at any position and any conservative amino acid substitution; and (iii) the motif GRAYLF (SEQ ID NO: 30), allowing for one amino acid substitution at any position and any conservative amino acid substitution. The nucleic acid to be introduced into a plant may be a Rill-length nucleic acid or may be a portion or a hybridizing sequence as hereinbefore defined.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company and Table 1 above).

According to a preferred feature of the invention, the homologue has at least 45% sequence identity to the amino acid sequence represented by SEQ ID NO: 2. Whether a polypeptide has at least 45% identity to the amino acid represented by SEQ ID NO: 2 may readily be established by sequence alignment. Methods for the alignment of sequences for comparison are well known in the art, such methods include GAP, BESTFIT, BLAST, FASTA and TFASTA. GAP uses the algorithm of Needleman and Wunsch (J. Mol. Biol. 48: 443-453, 1970) to find the alignment of two complete sequences that maximises the number of matches and minimises the number of gaps. The BLAST algorithm calculates percent sequence identity and performs a statistical analysis of the similarity between the two sequences. The software for performing BLAST analysis is publicly available through the National Centre for Biotechnology Information. A YIPPEE-like polypeptide or a homologue thereof having at least 45% identity to the amino acid represented by SEQ ID NO: 2 may readily be identified by aligning a query sequence (preferably a protein sequence) with known YIPPEE-like protein sequences (see for example the alignment shown in FIG. 1). The query sequence may be aligned (with known YIPPEE-like sequences) using, for example, the VNTI AlignX multiple alignment program, based on a modified clustal W algorithm (InforMax, Bethesda, Md. ), with default settings for gap opening penalty of 10 and a gap extension of 0.05.

Also encompassed by the term "homologues" are two special forms of homology, which include orthologous sequences and paralogous sequences, which encompass evolutionary concepts used to describe ancestral relationships of genes. The term "paralogous" relates to gene-duplications within the genome of a species leading to paralogous genes. The term "orthologous" relates to homologous genes in different organisms due to speciation.

Othologues in, for example, monocot plant species may easily be found by performing a so-called reciprocal blast search. This may be done by a first blast involving blasting the sequence in question (for example, SEQ ID NO: 1 or SEQ ID NO: 2) against any sequence database, such as the publicly available NCBI database which may be found at the NCBI website. If orthologues in rice were sought, the sequence in question would be blasted against, for example, the 28,469 full-length cDNA clones from *Oryza sativa* Nipponbare available at NCBI. BLASTn or tBLASTX may be used when starting from nucleotides or BLASTP or TBLASTN when starting from the protein, with standard default values. The blast results may be filtered. The full-length sequences of either the filtered results or the non-filtered results are then blasted back (second blast) against the sequences of the organism from which the sequence in question is derived. The results of the first and second blasts are then compared. An orthologue is found when the results of the second blast give as hits with the highest similarity an YIPPEE-like nucleic acid or YIPPEE-like polypeptide, for example, if one of the organisms is *Arabidopsis thaliana* then a paralogue is found. In the case of large families, ClustalW may be used, followed by a neighbour joining tree, to help visualize the clustering.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues. Preferably, amino acid substitutions comprise conservative amino acid substitutions.

A homologue may also be in the form of an "insertional variant" of a protein, i.e. where one or more amino acid residues are introduced into a predetermined site in a protein. Insertions may comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

Homologues in the form of "deletion variants" of a protein are characterised by the removal of one or more amino acids from a protein.

Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The YIPPEE-like polypeptide or homologue thereof may be a derivative. "Derivatives" include peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in SEQ ID NO: 2. "Derivatives" of a protein encompass peptides, oligopeptides, polypeptides, proteins and enzymes which may comprise naturally occurring altered, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

The YIPPEE-like polypeptide or homologue thereof may be encoded by an alternative splice variant of a YIPPEE-like nucleic acid/gene. The term "alternative splice variant" as used herein encompasses variants of a nucleic acid sequence in which selected introns and/or exons have been excised, replaced or added. Such variants will be ones in which the biological activity of the protein is retained, which may be achieved by selectively retaining functional segments of the protein. Such splice variants may be found in nature or may be manmade. Methods for making such splice variants are well known in the art. Preferred splice variants are splice variants of the nucleic acid represented by SEQ ID NO: 1. Further preferred are splice variants encoding a polypeptide comprising any one or more of and preferably all of: (i) a putative zinc-binding motif: 2xCXXC, where X is any amino acid residue; (ii) the motif KYKEGK (SEQ ID NO: 29), allowing for one amino acid substitution and any conservative amino acid substitution; (iii) the motif GRAYLF (SEQ ID NO: 30), allowing for one amino acid substitution and any conservative amino acid substitution.

The homologue may also be encoded by an allelic variant of a nucleic acid encoding a YIPPEE-like polypeptide or a homologue thereof, preferably an allelic variant of the nucleic acid represented by SEQ ID NO: 1. Further preferably, the polypeptide encoded by the allelic variant comprises any one or more of, and preferably all of (i) a putative zinc-binding motif: 2xCXXC, where X is any amino acid residue; (ii) the motif KYKEGK (SEQ ID NO: 29), allowing for one amino acid substitution at any position and any conservative amino acid substitution; (iii) the motif GRAYLF (SEQ ID NO: 30), allowing for one amino acid substitution at any position and any conservative amino acid substitution. Allelic variants exist in nature and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

According to a preferred aspect of the present invention, enhanced or increased expression of the YIPPEE-like nucleic acid or variant thereof is envisaged. Methods for obtaining enhanced or increased expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a YIPPEE-like nucleic acid or variant thereof. For example, endogenous promoters may be altered in vivo by mutation, deletion, and/or substitution (see, Kmiec, U.S. Pat. No. 5,565,350; Zarling et al., PCT/US93/

03868), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold, Buchman and Berg, Mol. Cell biol. 8:4395-4405 (1988); Callis et al., Genes Dev. 1:1183-1200 (1987). Such intron enhancement of gene expression is typically greatest when placed near the 5' end of the transcription unit. Use of the maize introns Adh1-S intron 1, 2, and 6, the Bronze-1 intron are known in the art. See generally, The Maize Handbook, Chapter 116, Freeling and Walbot, Eds., Springer, N.Y. (1994).

The invention also provides genetic constructs and vectors to facilitate introduction and/or expression of the nucleotide sequences useful in the methods according to the invention.

Therefore, there is provided a gene construct comprising:
(i) A YIPPEE-like nucleic acid or variant thereof;
(ii) One or more control sequences capable of driving expression of the nucleic acid sequence of (i); and optionally
(iii) A transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

Plants are transformed with a vector comprising the sequence of interest (i.e., a YIPPEE-like nucleic acid or variant thereof). The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence. The promoter may be an inducible promoter, i.e. having induced or increased transcription initiation in response to a developmental, chemical, environmental or physical stimulus. An example of an inducible promoter being a stress-inducible promoter, i.e. a promoter activated when a plant is exposed to various stress conditions. Additionally or alternatively, the promoter may be a tissue-preferred promoter, i.e. one that is capable of preferentially initiating transcription in certain tissues, such as the leaves, roots, seed tissue etc. Promoters able to initiate transcription in certain tissues only are referred to herein as "tissue-specific".

Preferably, the YIPPEE-like nucleic acid or variant thereof is operably linked to a constitutive promoter. A constitutive promoter is transcriptionally active during most, but not necessarily all, phases of its growth and development and is substantially ubiquitously expressed. Preferably, the constitutive promoter is a GOS2 promoter (from rice) (SEQ ID NO: 25). It should be clear that the applicability of the present invention is not restricted to the YIPPEE-like nucleic acid represented by SEQ ID NO: 1, nor is the applicability of the invention restricted to expression of an YIPPEE-like nucleic acid when driven by a GOS2 promoter. Examples of other constitutive promoters are shown in Table 4 below.

TABLE 4

Examples of constitutive promoters

| Gene Source | Expression Pattern | Reference |
|---|---|---|
| Actin | Constitutive | McElroy et al, Plant Cell, 2: 163-171, 1990 |
| CAMV 35S | Constitutive | Odell et al, Nature, 313: 810-812, 1985 |
| CaMV 19S | Constitutive | Nilsson et al., Physiol. Plant. 100: 456-462, 1997 |
| GOS2 | Constitutive | de Pater et al, Plant J Nov; 2(6): 837-44, 1992 |
| Ubiquitin | Constitutive | Christensen et al, Plant Mol. Biol. 18: 675-689, 1992 |
| Rice cyclophilin | Constitutive | Buchholz et al, Plant Mol Biol. 25(5): 837-43, 1994 |
| Maize H3 histone | Constitutive | Lepetit et al, Mol. Gen. Genet. 231: 276-285, 1992 |
| Actin 2 | Constitutive | An et al, Plant J. 10(1); 107-121, 1996 |

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences which may be suitable for use in performing the invention. Such sequences would be known or may readily be obtained by a person skilled in the art.

The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of the invention. Suitable markers may be selected from markers that confer antibiotic or herbicide resistance. Cells containing the recombinant DNA will thus be able to survive in the presence of antibiotic or herbicide concentrations that kill untransformed cells. Examples of selectable marker genes include the bar gene which provides resistance to the herbicide Basta; the npt gene which confers resistance to the antibiotic kanamycin; the hpt gene which confers hygromycin resistance. Visual markers, such as the Green Fluorescent Protein (GFP, Haseloff et al., 1997), β-glucuronidase (GUS) or luciferase may also be used as selectable markers. Further examples of suitable selectable marker genes include the ampicillin resistance (Ampr), tetracydine resistance gene (Tcr), phosphinothricin resistance gene, hygromycin resistance gene and the chloramphenicol acetyltransferase (CAT) gene, amongst others.

The present invention also encompasses plants obtainable by the methods according to the present invention. The present invention therefore provides plants obtainable by the method according to the present invention, which plants have introduced therein a YIPPEE-like nucleic acid or variant thereof and/or which plants have a genetic modification preferably in the locus of a YIPPEE-like gene.

The invention also provides a method for the production of transgenic plants having improved growth characteristics, comprising introduction and expression in a plant of a YIPPEE-like nucleic acid or a variant thereof and/or comprising introduction of a genetic modification preferably in the locus of a YIPPEE-like gene.

More specifically, the present invention provides a method for the production of transgenic plants having improved growth characteristics, which method comprises:
  (i) introducing into a plant or plant cell a YIPPEE-like nucleic acid or variant thereof and/or introducing a genetic modification preferably in the locus of a YIPPEE-like gene; and
  (ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. Transgenic rice plants expressing a YIPPEE-like nucleic acid/gene are preferably produced via *Agrobacterium*-mediated transformation using any of the well known methods for rice transformation, such as described in any of the following: published European patent application EP 1198985 A1, Aldemita and Hodges (Planta, 199, 612-617, 1996); Chan et al. (Plant Mol. Biol. 22 (3) 491-506, 1993), Hiei et al. (Plant J. 6 (2) 271-282, 1994), which disclosures are incorporated by reference herein as if fully set forth. In the case of corn transformation, the preferred method is as described in either Ishida et al. (Nat. Biotechnol. 1996 June; 14(6): 745-50) or Frame et al. (Plant Physiol. 2002 May; 129(1): 13-22), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention also includes host cells containing an isolated YIPPEE-like nucleic acid or variant thereof. Preferred host cells according to the invention are plant cells. The invention also extends to harvestable parts of a plant such as but not limited to seeds, leaves, fruits, flowers, stem cultures, rhizomes, tubers and bulbs.

The present invention also encompasses the use of YIPPEE-like nucleic acids or variants thereof and to the use of YIPPEE-like polypeptides or homologues thereof.

One such use relates to improving the growth characteristics of plants, in particular in improving yield/biomass, especially seed yield. The seed yield may include one or more of the following: increased number of (filled) seeds, increased seed weight, increased harvest index among others.

YIPPEE-like nucleic acids or variants thereof, or YIPPEE-like polypeptides or homologues thereof may find use in breeding programmes in which a DNA marker is identified which may be genetically linked to a YIPPEE-like gene or variant thereof. The YIPPEE-like nucleic acids/genes or variants thereof, or YIPPEE-like polypeptides or homologues thereof may be used to define a molecular marker. This DNA or protein marker may then be used in breeding programs to select plants having improved growth characteristics. The YIPPEE-like gene or variant thereof may, for example, be a nucleic acid as represented by any one of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 and SEQ ID NO: 23.

Allelic variants of a YIPPEE-like nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place by, for example, PCR. This is followed by a selection step for selection of superior allelic variants of the sequence in question and which give improved growth characteristics in a plant. Selection is typically carried out by monitoring growth performance of plants containing different allelic variants of the sequence in question, for example, different allelic variants of any one of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 and SEQ ID NO: 23. Growth performance may be monitored in a greenhouse or in the field. Further optional steps include crossing plants, in which the superior allelic variant was identified, with another plant. This could be used, for example, to make a combination of interesting phenotypic features.

A YIPPEE-like nucleic acid or variant thereof may also be used as probes for genetically and physically mapping the genes that they are a part of, and as markers for traits linked to those genes. Such information may be useful in plant breeding in order to develop lines with desired phenotypes. Such use of YIPPEE-like nucleic acids or variants thereof requires only a nucleic acid sequence of at least 15 nucleotides in length. The YIPPEE-like nucleic acids or variants thereof may be used as restriction fragment length polymorphism (RFLP) markers. Southern blots (Maniatis) of restriction-digested plant genomic DNA may be probed with the YIPPEE-like nucleic acids or variants thereof. The resulting banding patterns may then be subjected to genetic analyses using computer programs such as MapMaker (Lander et al. (1987) Genomics 1:174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the YIPPEE-like nucleic acid or variant thereof in the genetic map previously obtained using this population (Botstein et al. (1980) Am. J. Hum. Genet. 32:314-331).

The production and use of plant gene-derived probes for use in genetic mapping is described in Bematzky and Tanksley (1986) Plant Mol. Biol. Reporter 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7:149-154). Although current methods of FISH mapping favor use of large clones (several to several hundred KB; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

YIPPEE-like nucleic acids or variants thereof or YIPPEE-like polypeptides or homologues thereof may also find use as growth regulators. Since these molecules have been shown to be useful in improving the growth characteristics of plants, they would also be useful growth regulators, such as herbicides or growth stimulators. The present invention therefore provides a composition, for use as a growth regulator, comprising a YIPPEE-like nucleic acid/gene or variant thereof, or a YIPPEE-like polypeptide or homologue thereof, together with a suitable carrier, diluent or excipient.

The methods according to the present invention result in plants having improved growth characteristics, as described hereinbefore. These advantageous growth characteristics may also be combined with other economically advantageous traits, such as further yield-enhancing traits, tolerance to various stresses, traits modifying various architectural features and/or biochemical and/or physiological features.

DESCRIPTION OF FIGURES

The present invention will now be described with reference to the following figures in which:

FIG. 1 shows a multiple alignment of several plant YIPPEE-like polypeptides. The cysteine residues of the putative zinc-binding motif 2xCXXC, where X may be any amino acid, are in bold. The motif KYKEGK (SEQ ID NO: 29) and the motif GRAYLF (SEQ ID NO: 30) are boxed. At denotes *Arabidopsis thaliana*.

FIG. 3 details examples of sequences useful in performing the methods according to the present invention.

EXAMPLES

Figure 2:
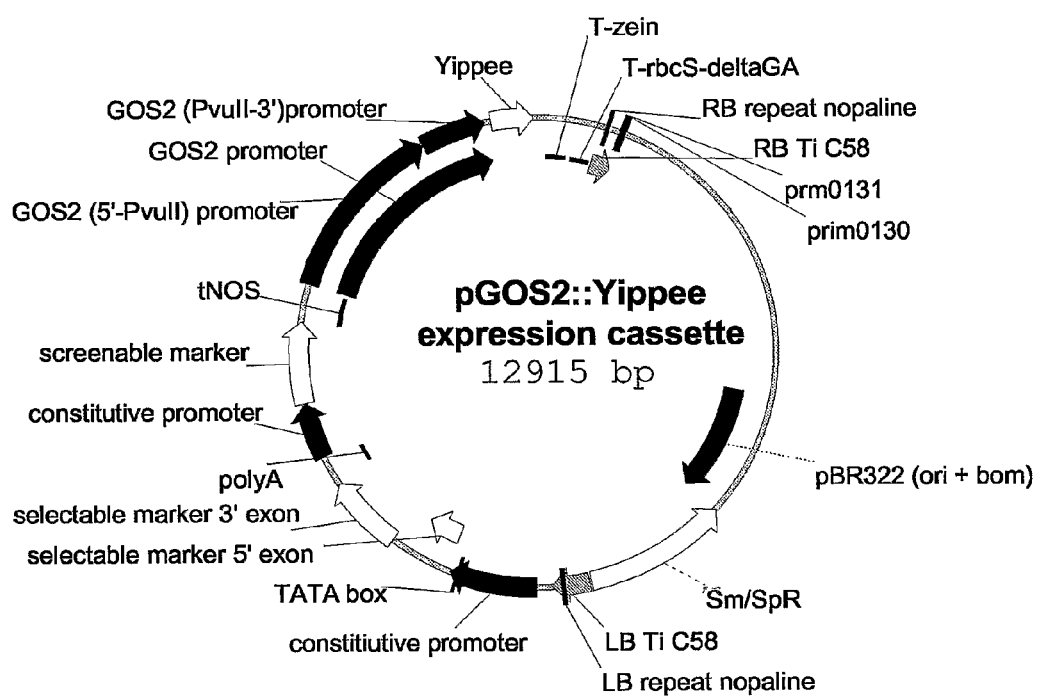
FIG. 2 shows a binary vector for expression in *Oryza sativa* of an *Arabidopsis thaliana* YIPPEE-like (internal reference CDS1522) under the control of a GOS2 promoter (internal reference PRO0129).

The present invention will now be described with reference to the following examples, which are by way of illustration alone.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al., (1994), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Gene Cloning

The *Arabidopsis thaliana* YIPPEE-like gene (CDS1522) was amplified by PCR using as template an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was 1.5 kb and the original number of clones was of the order of $1.59 \times 10^7$ cfu. Original titer was determined to be $9.6 \times 10^5$ cfu/ml after first amplification of $6 \times 10^{11}$ cfu/ml. After plasmid extraction, 200 ng of template was used in a 50 µl PCR mix. Primers prm03196 (sense, start codon in bold, AttB1 site in italic: 5'-GGGGACAAGTTTG-TACAAAAAAGCAGGCTTCACAATGGCT-GTCGGAGATGAT 3', SEQ ID NO: 28) and prm03199 (reverse, complementary, stop codon in bold, AttB2 site in italic: 5' GGGGACCACTTTGTACAAGAAAGCTGGG-TAATCAAGCATCATCTCCATCACTAAC 3', SEQ ID NO: 27), which include the AttB sites for Gateway recombination, were used for PCR amplification. PCR was performed using Hifi Taq DNA polymerase in standard conditions. A PCR fragment of 366 bp was amplified and purified also using standard methods. The first step of the Gateway procedure, the BP reaction, was then performed, during which the PCR fragment recombines in vivo with the pDONR201 plasmid to produce, according to the Gateway terminology, an "entry clone", p3956. Plasmid pDONR201 was purchased from Invitrogen, as part of the GATEWAY® technology.

Example 2

Vector Construction

The entry clone p3956 was subsequently used in an LR reaction with p0640, a destination vector used for *Oryza sativa* transformation. This vector contains as functional elements within the T-DNA borders: a plant selectable marker; a screenable marker expression cassette; and a Gateway cassette intended for LR in vivo recombination with the sequence of interest already cloned in the entry clone. A rice GOS2 promoter for constitutive expression (PRO0129) was upstream of this Gateway cassette (De Pater et al., Plant J. 1992 November; 2(6):837-44).

After the LR recombination step, the resulting expression vector (FIG. 2) was transformed into *Agrobacterium* strain LBA4044 and subsequently to *Oryza sativa* plants. Transformed rice plants were allowed to grow and were then examined for the parameters described in Example 3.

Example 3

Evaluation and Results

Approximately 15 to 20 independent T0 rice transformants were generated. The primary transformants were transferred from a tissue culture chamber to a greenhouse for growing and harvest of T1 seed. 5 events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression.

Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the presence or position of the gene that is causing the differences in phenotype.

3.1 Seed-Related Parameter Measurements

The mature primary panicles were harvested, bagged, barcode-labeled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. The harvest index in the present invention is defined as the ratio of total seed yield and the above ground area ($mm^2$) multiplied by a factor $10^6$.

3.2 Aboveground Area

Plant aboveground area was determined by counting the total number of pixels from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground.

The Table of results below show the p values from the F test for the T1 evaluations and for extra T1 events generated. The percentage difference between the transgenics and the corresponding nullizygotes is also shown. For example, for total seed weight, 3 out of 6 lines were positive for total seed weight (i.e., showed an increase in total seed weight (of greater than 32%) compared to the seed weight of corresponding nullizygote plants). 1 out of 6 of these lines showed a significant increase in total seed weight with a p value from the F test of 0.18.

TABLE 5

Results of the T1 generation

|  | Number of lines showing an increase | Difference | Number of lines showing a significant increase | p value of F test |
|---|---|---|---|---|
| Total seed weight | 3 out of 6 | >32% | 1 out of 6 | 0.18 |
| Total number of seeds | 1 out of 6 | >40% | 1 out of 6 | 0.17 |

TABLE 5-continued

Results of the T1 generation

|  | Number of lines showing an increase | Difference | Number of lines showing a significant increase | p value of F test |
|---|---|---|---|---|
| Number of filled seeds | 3 out of 6 | >49% | 3 out of 6 | 0.15 |
| Harvest Index | 2 out of 6 | >36% | 2 out of 6 | 0.064 |

TABLE 6

T1 extra events

|  | Number of lines showing a positive difference | Difference | Number of lines showing a significant difference | p value of F test |
|---|---|---|---|---|
| Total area | 2 out of 10 | >14% | 2 out of 10 | 0.16 |
| Total seed weight | 3 out of 10 | >44% | 2 out of 10 | 0.085 |
| Total number of seeds | 3 out of 10 | >16% | 2 out of 10 | 0.082 |
| Number of filled seeds | 5 out of 10 | >27% | 3 out of 10 | 0.088 |
| Harvest Index | 5 out of 10 | >22% | 2 out of 10 | 0.011 |

The invention claimed is:

1. A method for improving plant growth characteristics, comprising introducing and overexpressing in a plant a YIPPEE-like nucleic acid, wherein the YIPPEE-like nucleic acid encodes a YIPPEE-like polypeptide comprising:
   (i) a putative zinc-binding motif 2xCXXC, where X is any amino acid residue;
   (ii) a motif KYKEGK (SEQ ID NO: 29), allowing for one amino acid substitution at any position and any conservative amino acid substitution; and
   (iii) a motif GRAYLF (SEQ ID NO: 30), allowing for one amino acid substitution at any position and any conservative amino acid substitution,
   wherein said improved plant growth characteristics is increased yield relative to a corresponding wild type plant.

2. The method according to claim 1, wherein said YIPPEE-like nucleic acid is of plant origin.

3. The method according to claim 1, wherein said YIPPEE-like nucleic acid is operably linked to a constitutive promoter.

4. The method according to claim 3, wherein said constitutive promoter is a GOS2 promoter.

5. The method according to claim 1, wherein said increased yield is increased seed yield relative to a corresponding wild type plant.

6. The method according to claim 5, wherein said increased seed yield is selected from any one or more of (i) increased seed biomass (seed weight); (ii) increased number of (filled) seeds; (iii) increased seed size; (iv) increased seed volume; (v) increased harvest index; and (vi) increased thousand kernel weight (TKW).

7. The method according to claim 1, wherein said increased yield is increased plant biomass relative to a corresponding wild type plant.

8. A plant obtained by the method according to claim 1.

9. The method according to claim 1, wherein the YIPPEE-like polypeptide comprises:
   (i) the polypeptide sequence of SEQ ID NO: 2;
   (ii) a polypeptide sequence encoded by the nucleic acid sequence of SEQ ID NO: 1; or
   (iii) a polypeptide sequence having at least 45% sequence identity to the polypeptide sequence of SEQ ID NO: 2.

10. The method of claim 9, wherein the YIPPEE-like polypeptide comprises:
   (i) the polypeptide sequence of SEQ ID NO: 2, 4, 6, 8, 10, 12, 14, 16, 18, 20, 22, or 24; or
   (ii) a polypeptide sequence encoded by the nucleic acid sequence of SEQ ID NO: 1, 3, 5, 7, 9, 11, 13, 15, 17, 19, 21, or 23.

11. The method according to claim 1, wherein the putative zinc-binding motif 2xCXXC is found with a gap of about 52 amino acids residues between the first and second CXXC.

12. The method according to claim 1, wherein the YIPPEE-like nucleic acid comprises at least 249 nucleotides.

13. A plant transformed with a construct comprising:
   (i) a YIPPEE-like nucleic acid,
   (ii) one or more control sequences capable of driving expression of the YIPPEE-like nucleic acid, and optionally
   (iii) a transcription termination sequence,
   wherein the one or more control sequences capable of driving expression of the YIPPEE-like nucleic acid is a GOS2 promoter, and wherein the plant has increased yield relative to a corresponding wild type plant.

14. A method for the production of a transgenic plant having improved growth characteristics, wherein the method comprises:
(i) introducing and overexpressing in a plant a YIPPEE-like nucleic acid; and
(ii) cultivating the plant cell under conditions promoting plant growth and development
wherein said improved plant growth characteristics is increased yield relative to a corresponding wild type plant.

15. The method of claim 14, wherein said increased yield is increased plant biomass or increased seed yield relative to a corresponding wild type plant.

16. The method of claim 15, wherein said increased seed yield is selected from any one or more of (i) increased seed biomass (seed weight); (ii) increased number of (filled) seeds; (iii) increased seed size; (iv) increased seed volume; (v) increased harvest index; and (vi) increased thousand kernel weight (TKW).

17. A transgenic plant having improved growth characteristics resulting from overexpressing a YIPPEE-like nucleic acid introduced into said plant, wherein said improved plant growth characteristics is increased yield relative to a corresponding wild type plant.

18. The transgenic plant according to claim 17, wherein said transgenic plant is sugar cane, cereal, rice, maize, wheat, barley, millet, rye, oats, or sorghum.

19. Harvestable parts of the transgenic plant according to claim 17.

20. Harvestable parts according to claim 19, wherein said harvestable parts are seeds.

21. The transgenic plant of claim 17, wherein said increased yield is increased plant biomass or increased seed yield relative to a corresponding wild type plant.

22. The transgenic plant of claim 21, wherein said increased seed yield is selected from any one or more of (i) increased seed biomass (seed weight); (ii) increased number of (filled) seeds; (iii) increased seed size; (iv) increased seed volume; (v) increased harvest index; and (vi) increased thousand kernel weight (TKW).

* * * * *